US008969553B2

(12) United States Patent
Karig et al.

(10) Patent No.: US 8,969,553 B2
(45) Date of Patent: *Mar. 3, 2015

(54) METHOD FOR PRODUCING N-SULFONYL-SUBSTITUTED OXINDOLES

(75) Inventors: Gunter Karig, Hofheim am Taunus (DE); Mark James Ford, Schmitten (DE); Konrad Siegel, Düsseldorf (DE); Stefan Schnatterer, Hattersheim (DE)

(73) Assignee: Bayer Intellectual Property GmbH, Monheim (DE)

( * ) Notice: Subject to any disclaimer, the term of this patent is extended or adjusted under 35 U.S.C. 154(b) by 0 days.

This patent is subject to a terminal disclaimer.

(21) Appl. No.: 13/995,898

(22) PCT Filed: Dec. 19, 2011

(86) PCT No.: PCT/EP2011/073282
§ 371 (c)(1),
(2), (4) Date: Sep. 18, 2013

(87) PCT Pub. No.: WO2012/084854
PCT Pub. Date: Jun. 28, 2012

(65) Prior Publication Data
US 2014/0005388 A1 Jan. 2, 2014

Related U.S. Application Data

(60) Provisional application No. 61/467,598, filed on Mar. 25, 2011, provisional application No. 61/425,349, filed on Dec. 21, 2010.

(30) Foreign Application Priority Data

Dec. 21, 2010 (EP) .................................... 10196205
Mar. 25, 2011 (EP) .................................... 11159875

(51) Int. Cl.
*C07D 403/04* (2006.01)
*C07D 251/20* (2006.01)
*A01N 43/38* (2006.01)
*A01N 43/66* (2006.01)

(52) U.S. Cl.
CPC ............ *C07D 251/20* (2013.01); *C07D 403/04* (2013.01)
USPC ........... 544/180; 544/219; 544/218; 544/217; 544/238; 544/333; 544/336; 546/268.1; 504/230; 504/235; 504/236; 504/239; 504/244

(58) Field of Classification Search
CPC .............................. C07D 403/04; A01N 43/66
USPC .................... 544/180, 219; 504/230
See application file for complete search history.

(56) References Cited

U.S. PATENT DOCUMENTS

| 5,594,023 | A | 1/1997 | Wagnon et al. |
| 2004/0180878 | A1 | 9/2004 | Di Malta et al. |
| 2005/0070718 | A1 | 3/2005 | Lubisch et al. |
| 2008/0318923 | A1 | 12/2008 | Sekiguchi et al. |
| 2009/0318406 | A1 | 12/2009 | Geneste et al. |
| 2010/0069384 | A1 | 3/2010 | Foulon et al. |

FOREIGN PATENT DOCUMENTS

| FR | 2714378 A1 | 6/1995 |
| WO | 2006072458 A2 | 7/2006 |
| WO | 2006100080 A1 | 9/2006 |
| WO | 2006100081 A2 | 9/2006 |
| WO | 2006100082 A2 | 9/2006 |
| WO | 2006110917 A2 | 10/2006 |
| WO | 2008025735 A1 | 3/2008 |
| WO | 2008080970 A1 | 7/2008 |
| WO | 2008107399 A1 | 9/2008 |
| WO | 2009083559 A1 | 7/2009 |

OTHER PUBLICATIONS

International Search Report for PCT/EP2011/073282 Mailed May 3, 2012.
Bruce et al. "Heterocyclic Compound8 of Nitrogen. Part I. The Alkytation and Acyhtion of 3-Phenyloxindole, and the Preparation of Some Derivatives of 2-Hydroxy-3-phenylindole", J. Chem. Soc., (1957), pp. 4789-4798.
Ogata et al. "Synthesis and Antimycotic Properties of 3-(1-Imidazolyl)Indolin-2-Ones", Europ. Journal of Medicinal Chemistry (1981), vol. 16, pp. 373-3793.
Jiang et al. "Organocatalytic Asymmetric Allylic Alkylation of Oxindoles With Morita-Baylis-Hillman Carbonates", Chem. Communication (2009) vol. 26, pp. 3955-3957.
Hulme et al. "Quaternary Substituted PDE4 Inhibitors I: The Synthesis and in Vitro Evaluation of a Novel Series of Oxindoles", Biooranic & Medicinal Chemistry Letters (1998) vol. 8, pp. 175-178.
Blakemore P.R._N-Sulfonylation of Amides-Science of Synthesis, (2005) vol. 21, pp. 879-880.
Bhattacharya et al. "A New Class of Conjugated Strigolactone Analogues With Fluorescent Properties: Synthesis and Biological Activity", Organic & Biomolecular Chemistry (2009) vol. 7, pp. 3413.
Conway et al. "Studies on the Preparation of 2-Indolyl Triflates and Related Compounds", Synthetic Communications (1992) vol. 22, pp. 2987-2995.

*Primary Examiner* — Venkataraman Balasubramanian
(74) *Attorney, Agent, or Firm* — Miles & Stockbridge PC

(57) ABSTRACT

Process for the selective N-sulfonylation of oxindoles, in particular process for the N-sulfonylation of 3-triazinyloxindoles, and also N-sulfonyl-substituted 3-triazinyloxindoles and the use of N-sulfonyl-substituted oxindoles and of N-sulfonyl-substituted 3-triazinyloxindoles as intermediates for the synthesis of fine chemicals and of active ingredients in the field of pharmacy and agriculture, and also the use of these compounds as active ingredients in the field of agriculture.

16 Claims, No Drawings

METHOD FOR PRODUCING N-SULFONYL-SUBSTITUTED OXINDOLES

CROSS REFERENCE TO RELATED APPLICATIONS

This application is a §371 National Stage Application of PCT/EP2011/073282, filed Dec. 19, 2011, which claims priority to European Application No. 10196205.8, filed Dec. 21, 2010, U.S. Provisional Application No. 61/425,349, filed Dec. 21, 2010, European Application No. 11159875.1, filed Mar. 25, 2011, and U.S. Provisional Application No. 61/467, 598, filed Mar. 25, 2011.

BACKGROUND OF THE INVENTION

1. Field of the Invention

The present application relates to a process for the selective N-sulfonylation of oxindoles, in particular a process for the N-sulfonylation of 3-triazinyloxindoles, and also to the use thereof as intermediates for the synthesis of fine chemicals and of active ingredients in the field of agriculture.

2. Description of Related Art

Moreover, the present application relates to N-sulfonyl-substituted 3-triazinyloxindoles and their use as intermediates for the synthesis of fine chemicals in the field of agriculture.

The processes for the N-sulfonylation of oxindoles known from the prior art are often not aimed at carrying out the reaction on an industrial scale. Accordingly, the use of the activating agents used for processes known hitherto, in particular the bases used for the deprotonation, are not suitable for carrying out the reaction on an industrial scale.

Moreover, the prior art does not disclose a general principle for the as far as possible selective preparation of N-sulfonyl-substituted oxindoles. It is known that reactions for the sulfonylation of oxindoles can proceed unselectively depending on the reaction conditions, where (instead of the desired N-sulfonylated oxindole), an O-sulfonylated product or a disulfonylated, i.e. sulfonylated on the oxygen and on the nitrogen, product can be formed.

Examples for demonstrating the relatively low selectivity of the sulfonylation of oxindoles can be found e.g. in Synthetic Commun. (1992) 22, 2987 or Org. Biomol. Chem. (2009) 7, 3413. In this connection, it is assumed that the likelihood of the formation of O-sulfonylated products is increased particularly in the case of oxindoles in which at least one of the substituents in the 3 position is hydrogen.

Deprotonation

The deprotonation of the oxindole in the 1 position that precedes the sulfonylation is presumably an important prerequisite for the selectivity of the sulfonylation. The substitution of the oxindole backbone moreover, but especially the presence of a base serving as activating agent, can likewise be decisive for the progress of the sulfonylation.

It is known that hydrogen on heteroatoms in aliphatic, aromatic or heteroaromatic compounds can be replaced by functional substituents, such as e.g. a sulfonyl group. It is likewise known that N-unsubstituted or N-monosubstituted amides react with sulfonylation reagents such as sulfonyl chlorides in the presence of bases to give N-sulfonylamides.

Whereas amide sulfonylations can also be carried out with weak bases, such as e.g. pyridine or triethylamine, it is generally known (Blakemore, P. R.: N-Sulfonylation of Amides, Science of Synthesis, 21 (2005), p. 879), that the reaction is in most cases more successful if the deprotonation of the substrate is carried out with strong bases such as e.g. sodium hydride, butyllithium or lithium hexamethyldisilazane, in which case the deprotonation precedes the addition of the sulfonylation reagent to the nucleophilic amide anion that is produced on account of the deprotonation.

N-Sulfonyl-Substituted Oxindoles

Compounds which can be prepared in the manner specified in the preceding paragraph are e.g. optionally substituted oxindoles (1,3-dihydro-2H-indol-2-ones), in which, in the 1 position, hydrogen has been replaced by a sulfonyl substituent. These compounds are referred to as N-sulfonyl-substituted oxindoles.

Phenyl-Substituted Oxindoles

A subgroup of the N-sulfonyl-substituted oxindoles are those oxindoles which carry a phenyl substituent in the 3 position. Examples of syntheses of such compounds in which, in the 1 position, hydrogen has been replaced by a sulfonyl substituent can be found e.g. in FR 2714378, US 1997/5594023, US 2004/180878, US 2005/70718, WO 2006/110917, WO 2006/072458, WO 2006/100080, WO 2006/100081, WO 2006/100082, WO 2008/107399, WO 2008/025735, US 2008/318923, US 2009/318406, and in Bioorg. Med. Chem. Lett. (1998), 8, 175; Chem. Commun. (2009) 26, 3955.

A common feature of the reactions disclosed in the aforementioned prior art is that strong bases, such as sodium hydride or potassium tert-butylate, are used for the sulfonylation. However, these strong bases are sensitive to water and can therefore not be recovered undecomposed following an aqueous work-up. Moreover, these strong bases disadvantageously bring about the formation of equimolar amounts of elemental hydrogen and are therefore expensive. Consequently, the industrial use of these bases is not advantageous.

There are barely any examples in the prior art for the use of the weak base triethylamine for the sulfonylation of an oxindole which is substituted in the 3 position with phenyl and also imidazol-1-yl (European Journal of Medicinal Chemistry (1981), 16, 373). The chemical yield of the sulfonylation reaction from the aforementioned publication, however, is only 12% and is therefore unsuitable for use on an industrial scale (Example 1, variant F).

Hetaryl-Substituted Oxindoles

Oxindoles which carry a hetaryl substituent in the 3 position form a further subgroup of the N-sulfonyl-substituted oxindoles. Examples of reactions for obtaining N-sulfonyl-substituted oxindoles with a 6-ring hetaryl substituent in the 3 position, in which hydrogen in the 1 position is replaced by a sulfonyl substituent, are 3-(3-pyridyl)-substituted oxindoles (US 2005/70718, WO 2009/083559, WO 2008/80970), or 3-(3,5-pyrimidyl)-substituted oxindoles (US 2005/70718). However, it is also a common feature of the reactions disclosed in the aforementioned prior art that, for the sulfonylation, strong bases such as sodium hydride or potassium tert-butylate are used, the use of which on an industrial scale has the disadvantages described above.

N-Sulfonylation of Phenyl-Substituted Oxindoles with Sodium Carbonate

Scheme 1 summarizes a known process (J. Chem. Soc. (1957), 4789-4798) for the N-sulfonylation of an oxindole which carries a phenyl ring in the 3 position as a substituent. This process is notable for the fact that it is carried out not as in the reactions disclosed in the aforementioned prior art using strong bases such as sodium hydride or potassium tert-butylate, but with sodium carbonate as base in water/acetone. For the described reaction of 3-phenyloxindole A with 4-methylbenzenesulfonyl chloride, as product B 3-phenyl-1-toluene-p-sulfonyloxindole is given and a yield of 41% is specified.

Scheme 1-Reaction of 3-phenyloxindole with 4-methylbenzenesulfonyl chloride as sulfonylating agent:

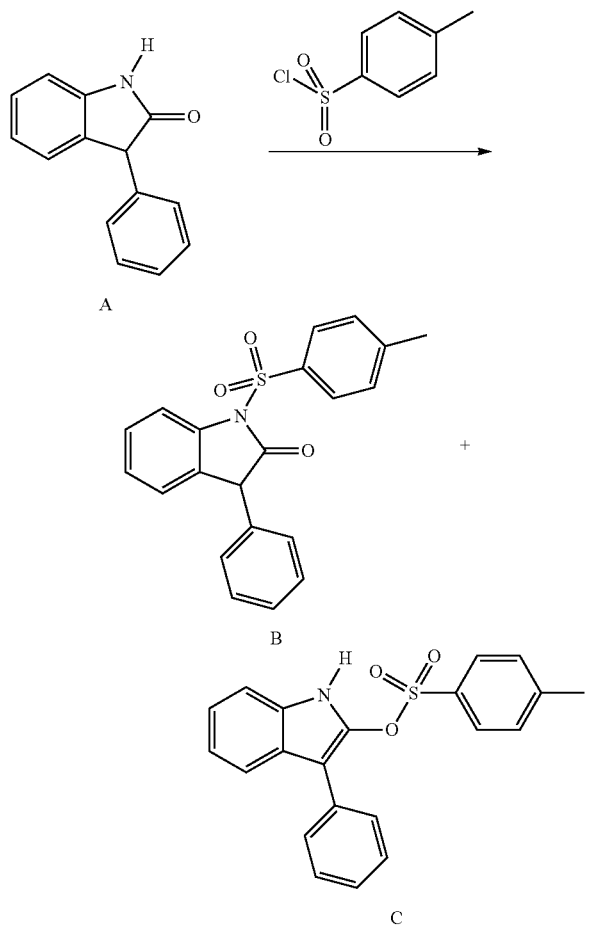

For comparison purposes, the reaction was reworked under the conditions described in J. Chem. Soc. (1957), 4789-4798 on page 4796 for the reaction of 3-phenyloxindole, using 4-methylbenzenesulfonyl chloride as sulfonylating agent, and sodium carbonate in water/acetone as base. Following product isolation, it was established by NMR analysis that in this reaction, the main component formed is not the N-sulfonylated product B, as postulated, but the O-sulfonylated product C (Example 11). Consequently, the process known from J. Chem. Soc. (1957), 4789 is not suitable for the preparation of N-sulfonyl-substituted 3-(phenyl)oxindoles.

N-Sulfonyl-Substituted 3-Triazinyloxindoles

N-Sulfonyl-substituted 3-triazinyloxindoles, which form a further subgroup of the N-sulfonyl-substituted oxindoles hetaryl-substituted in the 3 position are not described in the prior art. This is also true for processes for the preparation of N-sulfonyl-substituted 3-triazinyloxindoles.

One group of the N-sulfonyl-substituted 3-triazinyloxindoles that is particularly important from an economical point of view is those compounds which carry, as substituents of the N-sulfonyl group, completely or partially fluorine-substituted $C_1$-$C_6$ alkyl groups, in particular difluoromethyl and trifluoromethyl, or ($C_3$-$C_7$)-cycloalkyl groups. These compounds are suitable as active ingredients in pharmacy or agriculture or as intermediates for producing fine chemicals and active ingredients in the field of pharmacy or agriculture.

Again for comparison purposes, the conditions described in J. Chem. Soc. (1957), 4789-4798, on page 4796, were also applied to a 3-(triazinyl)oxindole during the reaction with 4-methylbenzenesulfonyl chloride. However, it was detected, by UV absorption and NMR analysis, that, likewise, it was not the N-sulfonylated product which is formed, but the O-sulfonylated product (Example 13). Consequently, the described process is likewise unsuitable for preparing N-sulfonyl-substituted 3-triazinyloxindoles.

N-Sulfonylation of Phenyl-Substituted Oxindoles with Sodium Hydride

US 2009/0318406 discloses a process for the sulfonylation in the 1 position of an oxindole which carries, as substituents in the 3 position, a substituted phenyl ring or a substituted piperazine ring. The process is carried out using sodium hydride as base in tetrahydrofuran as solvent at 0° C.

Again for comparison purposes, the conditions described in US 2009/0318406 on page 19, paragraph 243, were also applied to the reaction of a 3-triazinyloxindole with difluoromethanesulfonyl chloride. However, it was established that after a reaction time of 12 hours, virtually no conversion to the desired product had taken place (Example 1, variant D). Consequently, the process described in US 2009/0318406 is not suitable for preparing N-sulfonyl-substituted 3-triazinyloxindoles on an industrial scale, at least if difluoromethanesulfonyl chloride is used as sulfonylating agent.

N-Sulfonylation of Phenyl-Substituted Oxindoles with Potassium Tert-Butylate

US 2010/69384 discloses a process for the sulfonylation in the 1 position of an oxindole which carries, as substituents in the 3 position, a substituted phenyl ring and a methyl group. The process is carried out using potassium tert-butylate as base in tetrahydrofuran as solvent at −30° C.

Again for comparison purposes, the conditions described in US 2010/69384 on page 15, Example 7A, were also applied to the reaction of a 3-(triazinyl)oxindole with difluoromethanesulfonyl chloride. However, it was established that, after a reaction time of 12 hours, virtually no conversion to the desired product had taken place (Example 1, variant E). Consequently, the process described in US 2010/69384 is also not suitable for preparing N-sulfonyl-substituted 3-triazinyloxindoles, at least if difluoromethanesulfonyl chloride is used as sulfonylating agent.

The process for the sulfonylation of an oxindole substituted in the 3 position with phenyl and also imidazol-1-yl disclosed in European Journal of Medicinal Chemistry (1981), 16, 373 has already been discussed. The process is notable for the use of triethylamine as base with dichloromethane as solvent.

Again for comparison purposes, the conditions described in Journal of Medicinal Chemistry (1981), 16, 373 were also applied to the reaction of a 3-(triazinyl)oxindole with difluoromethanesulfonyl chloride. However, it was established that, after a reaction time of 3 hours and being left to stand for 15 hours, virtually no conversion to the desired product had taken place (Example 1, variant F). Consequently, the described process is not suitable for preparing N-sulfonyl-substituted 3-triazinyloxindoles, at least if difluoromethanesulfonyl chloride is used as sulfonylating agent.

SUMMARY

Against this background, the object of the invention is to provide the most selective possible process for obtaining N-sulfonyl-substituted oxindoles which carry a six-membered heteroaryl radical in the 3 position on an industrial scale.

Surprisingly, it has now been found that N-sulfonyl-substituted 3-triazinyloxindoles (3-1) can be prepared with good to very good selectivity by replacing a hydrogen atom in the 1 position of an optionally substituted 3-triazinyloxindole (1) with a sulfonyl compound (2), which carries a suitable leaving group X, in the presence of imidazole substituted in the 1 position or a mixture of imidazoles substituted in the 1 position with tertiary amine bases or a mixture of imidazoles substituted in the 1 position with substituted pyridine bases (Scheme 2).

Scheme 2-Synthesis of N-sulfonyl-substituted 3-triazinyloxindoles (3-1):

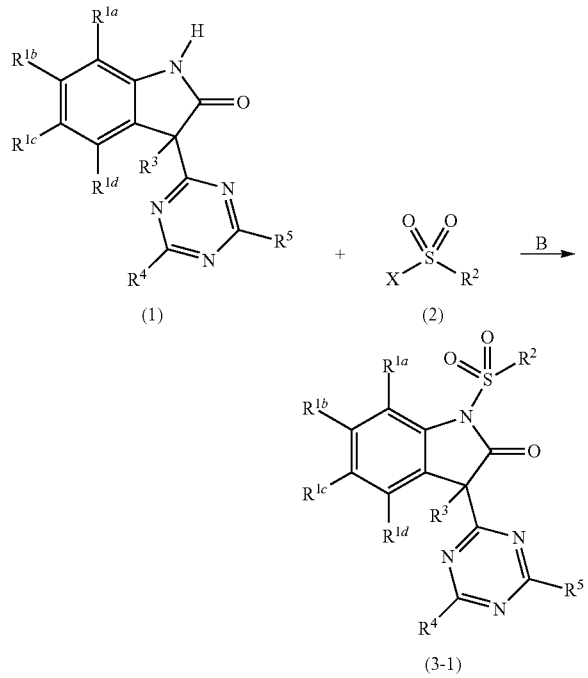

(1) = 3-(Triazinyl)oxindole
(2) = Sulfonylating agent
B = Imidazole base substituted in the 1 position or a base mixture comprising imidazole base substituted in the 1 position Imidazoles have, in their effect as bases, the advantage that they are suitable for use on an industrial scale because they are not decomposable, especially in the presence of water, and moreover do not produce equimolar amounts of hydrogen. Consequently, the object is achieved by a process for the preparation of N-sulfonyl-substituted oxindoles of the formula (3) which have a 6-ring heteroaryl substituent (Q) in the 3 position,

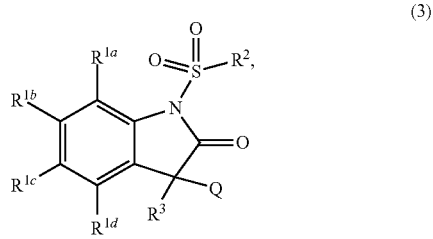

in which
$R^{1a}$ to $R^{1d}$, independently of one another, are selected from the group consisting of
hydrogen, fluorine, chlorine, bromine, iodine, and also from $(C_1-C_6)$-alkyl, where the alkyl radical is branched or unbranched and is unsubstituted or is substituted by one or more substituents selected from the group consisting of fluorine, chlorine, $(C_1-C_4)$-alkoxy or $(C_3-C_7)$-cycloalkyl, $(C_3-C_7)$-cycloalkyl, where the cycloalkyl radical is unsubstituted or is substituted by one or more substituents selected from the group consisting of fluorine, chlorine, $(C_1-C_4)$-alkyl or $(C_3-C_7)$-cycloalkyl or $(C_1-C_4)$-alkoxy, $(C_1-C_6)$-alkoxy, where the alkoxy radical is branched or unbranched and is unsubstituted or is substituted by one or more substituents selected from the group consisting of fluorine, chlorine, $(C_1-C_4)$-alkoxy or $(C_3-C_7)$-cycloalkyl, $(C_3-C_7)$-cycloalkoxy, where the cycloalkoxy radical is unsubstituted or is substituted by one or more substituents selected from the group consisting of fluorine, chlorine, $(C_1-C_4)$-alkyl or $(C_1-C_4)$-alkoxy, $(C_1-C_6)$-alkylthio, where the alkylthio radical is branched or unbranched and is unsubstituted or is substituted by one or more substituents selected from the group consisting of fluorine, chlorine, $(C_1-C_4)$-alkyl or $(C_1-C_4)$-alkoxy, $(C_3-C_7)$-cycloalkylthio, where the cycloalkylthio radical is unsubstituted or is substituted by one or more substituents selected from the group consisting of fluorine, chlorine, $(C_1-C_4)$-alkyl or $(C_1-C_4)$-alkoxy, and phenyl or 1-naphthyl or 2-naphthyl or a five- or six-membered heteroaromatic ring having 1 to 2 heteroatoms, where the heteroatoms are selected, independently of one another, from the group consisting of O or N and where the aryl or heteroaryl radical is unsubstituted or is substituted by one or more substituents selected from the group consisting of fluorine, chlorine, bromine, iodine, $(C_1-C_4)$-alkyl, $(C_1-C_4)$-alkoxy or $(C_3-C_7)$-cycloalkyl or $(C_1-C_4)$-alkylthio, and $R^2$ is
$(C_1-C_6)$-alkyl, where the alkyl radical is unsubstituted or is completely or partially substituted with fluorine, or
$(C_3-C_7)$-cycloalkyl, where the cycloalkyl radical is unsubstituted or is completely or partially substituted with fluorine, $R^3$ is
hydrogen or
$(C_1-C_6)$-alkyl, where the alkyl radical is branched or unbranched and is unsubstituted or is substituted by one or more substituents selected from the group consisting of fluorine, chlorine, $(C_1-C_4)$-alkoxy or $(C_3-C_7)$-cycloalkyl,
$(C_1-C_6)$-alkylthio, where the alkylthio radical is unsubstituted or is substituted by one or more substituents selected from the group consisting of fluorine, chlorine, $(C_1-C_4)$-alkyl or $(C_1-C_4)$-alkoxy,
and Q is
a six-membered heteroaromatic ring having 1 to 3 nitrogen atoms, where the heteroaromatic ring is unsubstituted or is substituted by one or more substituents selected from the group consisting of $(C_1-C_4)$-alkyl, $(C_1-C_4)$-alkoxy or $(C_3-C_7)$-cycloalkyl or $(C_3-C_7)$-cycloalkoxy or $(C_1-C_4)$-alkylthio, by reaction of an oxindole compound of the formula (1)

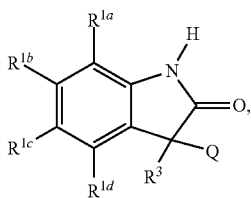

in which
R$^{1a}$ to R$^{1d}$, and R$^3$ and Q are as defined in formula (3),
in a solvent with a sulfonyl compound (2)

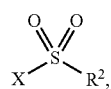

in which
R$^2$ is as defined in formula (3), and
X, as leaving group, is
  fluorine, chlorine, bromine, 1-imidazolyl, 1H-benzot-riazolyloxy, 1H-benzotriazolyl or
  O—SO$_2$—R$^7$, where R$^7$ is defined as R$^2$ and R$^2$ and R$^7$ are identical or different, or
  N(R$^8$)SO$_2$R$^9$, where R$^8$ is carbonyl and R$^9$ is unsubstituted or substituted phenyl, and R$^8$ and R$^9$ are bonded with one another or are not bonded,
  where the reaction is carried out in the presence of an imidazole base substituted in the 1 position, or a base mixture which comprises at least one imidazole base substituted in the 1 position.

DETAILED DESCRIPTION OF A PREFERRED EMBODIMENT

The heteroaryls falling in formula (1) under the definition of Q include in particular 1,3,5-triazin-2-yl.

The N-sulfonyl-substituted 3-triazinyloxindoles and the 3-triazinyloxindoles used in the process according to the invention are characterized in addition to the triazine radical in each case by the radical R$^2$, which represents a uniform feature for the compounds of the present invention.

The bases used do not decompose in the presence of water and do not release hydrogen (H$_2$) during the reaction, as is the case, for example, with sodium hydride.

Conversion

Moreover, it is surprising that specifically imidazole bases substituted in the 1 position considerably improve the selectivity of the N-sulfonylation compared with the O-sulfonylation of oxindoles which carry a six-membered heteroaryl radical in the 3 position. This is true particularly for obtaining N-sulfonyl-substituted 3-triazinyloxindoles.

It has been shown that a particular advantage of using imidazole bases in connection with the present process is that the bases are able to catalyze the complete or partial conversion of an O-sulfonylated hetaryl-substituted oxindole (D) formed in the course of the reaction as the main component or secondary component, or of another intermediate, to give the desired corresponding N-sulfonylated oxindole (C).

The conversion for a 3-triazinyloxindole is illustrated by Scheme 3 and Tables 1 and 2, and also demonstrated by way of example by Example 1, variant B.

Scheme 3-Conversion during the sulfonylation of a 3-triazinyloxindole:

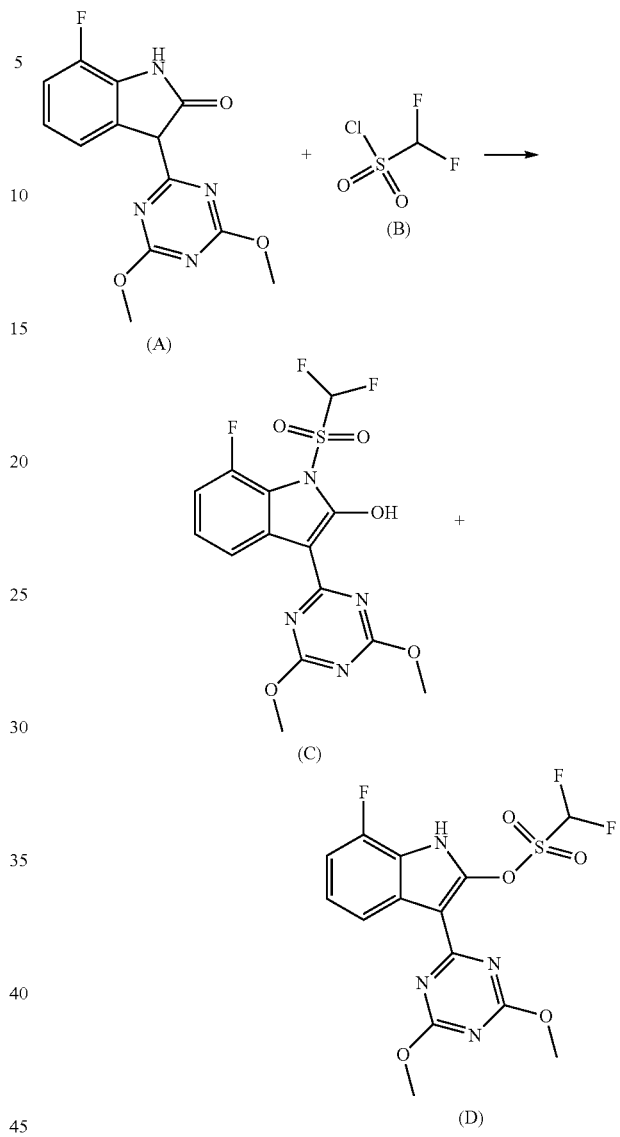

The conversion of a formed O-sulfonylated 3-triazinyloxindole (D) to give the desired N-sulfonylated 3-triazinyloxindole (C) takes place either
  directly, i.e. the desired N-sulfonylated 3-triazinyloxindole (C) is formed directly (Example 1, variant B), or
  indirectly, i.e. following the back-formation of the starting material (A), the desired N-sulfonylated 3-triazinyloxindole (C) is formed.

To demonstrate the conversion of an O-sulfonylated 3-triazinyloxindole (D) to give the desired N-sulfonylated 3-triazinyloxindole (C), a mixture consisting of 62% O-sulfonylated 3-triazinyloxindole (D) and of 30% N-sulfonylated 3-triazinyloxindole (C) is firstly isolated. (The fractions of compounds A, C, D in the overall mixture are determined by means of HPLC.)

The one half of the isolated mixture is reacted in the absence of the sulfonylation reagent difluoromethanesulfonyl chloride (B) with the imidazole base 1-methyl-1H-imidazole (see Table 1).

For comparison, the second half of the isolated mixture comprising 62% O-sulfonylated 3-triazinyloxindole (D) and comprising 30% N-sulfonylated 3-triazinyloxindole (C) is stirred without 1-methyl-1H-imidazole and in the absence of the sulfonylation reagent difluoromethanesulfonyl chloride (B) at 0° C. (see Table 2).

TABLE 1

(following the addition of 1-methyl-1H-imidazole)

| HPLC after | A | C | D | T° |
|---|---|---|---|---|
| 0 min | 1% | 30% | 62% | 0° C. |
| 1 h | 5% | 27% | 58% | 0° C. |
| 3 h | 9% | 31% | 52% | 0° C. |
| 7 h | 18% | 37% | 38% | 0° C. |
| over night | 22% | 58% | 12% | RT |

The results summarized in Table 1 show that, in the presence of 1-methyl-1H-imidazole, a conversion of O-sulfonylated 3-triazinyloxindole (D) to give the desired N-sulfonylated 3-triazinyloxindole (C) takes place.

The content of the desired N-sulfonylated 3-triazinyloxindole (C) increases, starting from 30% to 58%, i.e. the imidazole-catalyzed conversion leads almost to a doubling of N-sulfonylated 3-triazinyloxindole (C).

TABLE 2

(without the addition of 1-methyl-1H-imidazole)

| HPLC after | A | C | D | T° |
|---|---|---|---|---|
| 0 min | 1% | 30% | 62% | 0° C. |
| 1 h | 1% | 27% | 65% | 0° C. |
| 3 h | 2% | 31% | 61% | 0° C. |
| 7 h | 1% | 27% | 65% | 0° C. |
| over night | 2% | 30% | 62% | RT |

The results summarized in Table 2 show that the desired conversion of O-sulfonylated 3-triazinyloxindole (D) to give the desired N-sulfonylated 3-triazinyloxindole (C) does not take place without the addition of 1-methyl-1H-imidazole.

As regards the compounds according to the invention, other names used above and below are explained in summary. These are familiar to the person skilled in the art and have in particular the meanings explained below:

Where reference is made in this application to a "3-triazinyloxindole", one of the compounds encompassed by formula (I-1) is intended.

The 3-triazinyloxindoles (1-1) preferably used as starting materials

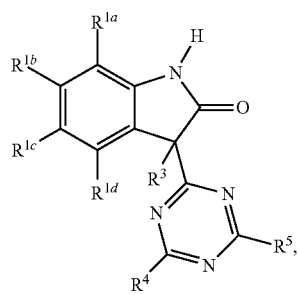

(1-1)

in which the radicals $R^{1a}$ to $R^{1d}$, $R^3$, $R^4$ and $R^5$ are as defined above, can be prepared using the processes known to the person skilled in the art.

Where reference is made in this application to a "sulfonyl compound", one of the compounds encompassed by the formula (2)

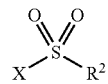

(2)

is intended. In compounds of the formula (2), $R^2$ and X are as defined above. The sulfonyl compounds (2) used as starting materials are known or can be prepared using methods known to the person skilled in the art.

Where reference is made in this application to a "tertiary amine base", one of the compounds encompassed by the formula (4)

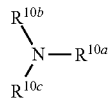

(4)

is intended, where
$R^{10a}$, $R^{10b}$ and $R^{10c}$, independently of one another, are branched or unbranched ($C_1$-$C_6$)-alkyl, and at least one of the substituents $R^{10a}$, $R^{10b}$ and $R^{10c}$ in a non-terminal position contains a further heteroatom such as oxygen or sulfur or the group $NR^{10d}$, where $R^{10d}$ is ($C_1$-$C_6$)-alkyl, or
$R^{10b}$ and $R^{10c}$ with one another are bonded to a three- to ten-membered ring, and the ring can contain at least one further heteroatom such as oxygen or sulfur or the group $NR^{10d}$, where $R^{10d}$ is ($C_1$-$C_6$)-alkyl, or
$R^{10a}$, $R^{10b}$ and $R^{10c}$ together form a bicycle, where the nitrogen atom present in formula (4) forms the one bridgehead atom, and the other bridgehead atom can be carbon or nitrogen, and in the case that the other bridgehead atom is carbon, one or both rings also contain at least one further heteroatom such as oxygen or sulfur or the group $NR^{10d}$, where $R^{10d}$ is ($C_1$-$C_6$)-alkyl, and ring atoms can also be bonded via a double bond.

If a compound of the formula (4) contains more than one heteroatom, then the heteroatoms cannot be directly next to one another.

Where reference is made in this application to a "substituted pyridine base", one of the compounds encompassed by the formula (5)

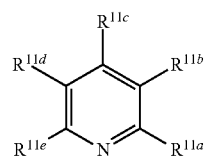

(5)

is intended, where
$R^{11a}$, $R^{11b}$, $R^{11c}$, $R^{11d}$ and $R^{11e}$, independently of one another, are hydrogen, methyl, ethyl, propyl or isopropyl and at least one of the substituents $R^{11a}$, $R^{11b}$, $R^{11c}$, $R^{11d}$ and $R^{11e}$ is not hydrogen.

The designation "halogen" means, for example, fluorine, chlorine, bromine or iodine. If the designation is used for a radical, then "halogen" means, for example, a fluorine, chlorine, bromine or iodine atom.

Alkyl means a straight-chain or branched open-chain, saturated hydrocarbon radical.

The expression "($C_1$-$C_4$)alkyl" means a shorthand for alkyl having one to 4 carbon atoms corresponding to the range given for carbon atoms, i.e. includes the radicals methyl, ethyl, 1-propyl, 2-propyl, 1-butyl, 2-butyl, 2-methylpropyl or tert-butyl. General alkyl radicals with a larger stated range of carbon atoms, e.g. "($C_1$-$C_6$)alkyl", correspondingly also includes straight-chain or branched alkyl radicals having a larger number of carbon atoms, i.e. according to the example, also the alkyl radicals having 5 and 6 carbon atoms.

Cycloalkyl means a carbocyclic, saturated ring system having preferably 3-8 ring carbon atoms, e.g. cyclopropyl, cyclobutyl, cyclopentyl or cyclohexyl. In the case of optionally substituted cycloalkyl, cyclic systems with substituents are included, in which case also substituents with a double bond on the cycloalkyl radical, e.g. an alkylidene group such as methylidene, are included.

In the case of optionally substituted cycloalkyl, polycyclic aliphatic systems are also included, such as, for example, bicyclo[1.1.0]butan-1-yl, bicyclo[1.1.0]butan-2-yl, bicyclo[2.1.0]pentan-1-yl, bicyclo[2.1.0]pentan-2-yl, bicyclo[2.1.0]pentan-5-yl, bicyclo[2.2.1]hept-2-yl (norbornyl), adamantan-1-yl and adamantan-2-yl.

In the case of substituted cycloalkyl, spirocyclic aliphatic systems are also included, such as, for example, spiro[2.2]pent-1-yl, spiro[2.3]hex-1-yl, spiro[2.3]hex-4-yl, 3-spiro[2.3]hex-5-yl.

Aryl means a mono-, bi- or polycyclic aromatic system having preferably 6 to 14, in particular 6 to 10, ring carbon atoms, for example phenyl, naphthyl, anthryl, phenanthrenyl, and the like, preferably phenyl.

Also included by the term "optionally substituted aryl" are polycyclic systems, such as tetrahydronaphthyl, indenyl, indanyl, fluorenyl, biphenylyl, where the bonding site is on the aromatic system.

From a systematic point of view, aryl is usually also included by the term "optionally substituted phenyl".

Alkoxy means an alkyl radical bonded via an oxygen atom, alkenyloxy means an alkenyl radical bonded via an oxygen atom, alkynyloxy means an alkynyl radical bonded via an oxygen atom, cycloalkyloxy means a cycloalkyl radical bonded via an oxygen atom and cycloalkenyloxy means a cycloalkenyl radical bonded via an oxygen atom.

Alkylthio means an alkyl radical bonded via a sulfur atom, alkenylthio means an alkenyl radical bonded via a sulfur atom, alkynylthio means an alkynyl radical bonded via a sulfur atom, cycloalkylthio means a cycloalkyl radical bonded via a sulfur atom and cycloalkenylthio means a cycloalkenyl radical bonded via a sulfur atom.

Haloalkyl, haloalkenyl and haloalkynyl mean alkyl, alkenyl or alkynyl, respectively, partly or completely substituted by identical or different halogen atoms, e.g. monohaloalkyl such as $CH_2CH_2Cl$, $CH_2CH_2F$, $CHClCH_3$, $CHFCH_3$, $CH_2Cl$, $CH_2F$; perhaloalkyl such as $CCl_3$ or $CF_3$ or $CF_2CF_3$; polyhaloalkyl such as $CHF_2$, $CH_2F$, $CH_2CHFCl$, $CHCl_2$, $CF_2CF_2H$, $CH_2CF_3$; haloalkoxy is e.g. $OCF_3$, $OCHF_2$, $OCH_2F$, $OCF_2CF_3$, $OCH_2CF_3$ and $OCH_2CH_2Cl$; the same applies to haloalkenyl and other radicals substituted by halogen.

Unless defined otherwise, the definition "is substituted with one or more radicals" means, independently of one another, one or more identical or different radicals, where two or more radicals on one cycle as basic bodies can form one or more rings.

Substituted radicals, such as a substituted alkyl, cycloalkyl, cycloalkenyl, aryl, phenyl, benzyl, heterocyclyl and heteroaryl radical, mean, for example, a substituted radical derived from the unsubstituted basic body, where the substituents are, for example, one or more, preferably 1, 2 or 3, radicals from the group halogen, alkoxy, alkylthio, hydroxy, amino, nitro, carboxy or a group equivalent to the carboxy group, cyano, isocyano, azido, alkoxycarbonyl, alkylcarbonyl, formyl, carbamoyl, mono- and dialkylaminocarbonyl, substituted amino, such as acylamino, mono- and dialkylamino, trialkylsilyl and optionally substituted cycloalkyl, optionally substituted aryl, optionally substituted heterocyclyl, where each of the last-mentioned cyclic groups can also be bonded via heteroatoms or divalent functional groups as in the case of the specified alkyl radicals, and alkylsulfinyl, where both enantiomers of the alkylsulfinyl group are included, alkylsulfonyl, alkylphosphinyl, alkylphosphonyl and, in the case of cyclic radicals (="cyclic basic body"), also mean alkyl, haloalkyl, alkylthioalkyl, alkoxyalkyl, optionally substituted mono- and dialkylaminoalkyl and hydroxyalkyl.

In the term "substituted radicals", such as substituted alkyl etc., besides the specified saturated hydrocarbon-containing radicals, corresponding unsaturated aliphatic and aromatic radicals, such as optionally substituted alkenyl, alkynyl, alkenyloxy, alkynyloxy, alkenylthio, alkynylthio, alkenyloxycarbonyl, alkynyloxycarbonyl, alkenylcarbonyl, alkynylcarbonyl, mono- and dialkenylaminocarbonyl, mono- and dialkynylaminocarbonyl, mono- and dialkenylamino, mono- and dialkynylamino, trialkenylsilyl, trialkynylsilyl, optionally substituted cycloalkenyl, optionally substituted cycloalkynyl, phenyl, phenoxy etc. are included as substituents. In the case of substituted cyclic radicals with aliphatic moieties in the ring, cyclic systems with those substituents which are bonded to the ring with a double bond, e.g. are substituted with an alkylidene group such as methylidene or ethylidene or an oxo group, imino group or substituted imino group, are also included.

The in each case unsubstituted or substituted radicals can be branched or unbranched. Thus, for example, a radical referred to as "$C_4$-alkyl" includes, as well as the unbranched butyl radical, all other $C_4$ isomers, including tert-butyl.

If two or more radicals form one or more rings, then these may be carbocyclic, heterocyclic, saturated, partially saturated, unsaturated, for example also aromatic and optionally further substituted. The fused rings are preferably 5- or 6-membered rings, particular preference being given to benzofused cycles.

In one preferred embodiment, $R^2$ is ($C_1$-$C_6$)-alkyl or ($C_3$-$C_7$)-cycloalkyl, where the alkyl radical or the cycloalkyl radical is completely or partly substituted with fluorine and where compounds of the formula (3-1) in which
 $R^{1a}$ is fluorine and
 $R^2$ is 2,2,-difluoroethyl or 1,1,1-trifluoroethyl are excluded, because the formation of these specific compounds could not be demonstrated under the reaction conditions described in this application. However, this does not exclude the fact that these compounds can be prepared e.g. by varying the composition of the base mixture, or by varying the reaction temperature or the pressure prevailing during the reaction.

In the aforementioned preferred embodiment,
$R^4$ and $R^5$, independently of one another, are in each case hydrogen,
 ($C_1$-$C_6$)-alkyl, where the alkyl radical is unsubstituted or is substituted by one or more substituents selected from the group consisting of fluorine, chlorine, ($C_1$-$C_4$)-alkoxy or ($C_3$-$C_7$)-cycloalkyl,
 ($C_1$-$C_6$)-alkoxy, where the alkoxy radical is branched or unbranched and is unsubstituted or is substituted by one or more substituents selected from the group consisting of fluorine, chlorine, (C$_1$-C$_4$)-alkoxy or (C$_3$-C$_7$)-cycloalkyl.

In a further preferred embodiment, R$^3$=H. In this case, compounds of the formula (3-1) can be present completely or partially also in the tautomeric enol form or as salts (3-1a)

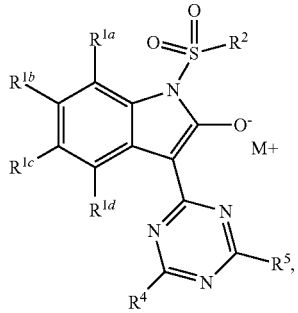

(3-1a)

in which
R1$^a$ to R1$^d$, and R$^2$, R$^4$ and R$^5$ are as defined above and M is Li, Na, K, Cs, Ba, Mg, Ca, Zn or N(R$^e$)$_4$ where R$^e$=H or C$_1$-C$_6$-alkyl, and the number of counterions M$^+$ is determined by the particular charge, such that the compound of the formula (3-1a) is neutral overall.

In a most preferred embodiment, difluoromethanesulfonyl chloride is used as sulfonylating agent, i.e. R$^2$ is difluoromethyl.

The imidazole bases used according to the invention are preferably
 1-(C$_1$-C$_6$)-alkyl-1H-imidazole,
 1-(C$_1$-C$_7$)-cycloalkyl-1H-imidazole,
 1-benzyl-1H-imidazole,
 1-aryl-1H-imidazole
 1-hetaryl-1H-imidazole, or
 a mixture which comprises at least two of the specified imidazole bases substituted in the 1 position.

The imidazole bases are particularly preferably 1-methyl-1H-imidazole, 1-butyl-1H-imidazole or 1-benzyl-1H-imidazole, which can be used individually or in a mixture, with the use of 1-methyl-1H-imidazole being very particularly preferred.

Compared with other bases, such as e.g. the bases sodium hydride or potassium tert-butylate described in the prior art, these bases have the advantage that they do not produce equimolar amounts of hydrogen or are not decomposed upon contact with water and are therefore suitable for use on an industrial scale.

Tertiary amine bases or substituted pyridine bases by themselves do not lead to an N-sulfonylation of the starting material. For example, it was shown that during the sulfonylation using trifluoromethanesulfonic anhydride with 1-methyl-1H-imidazole as base, the N-sulfonylated product is formed (Example 9), whereas the use of 1,4-diazabicyclo[2.2.2]octane (DABCO) as base leads preferentially to the O-sulfonylated product (Example 10). The distinction between the N- and O-sulfonylation can take place by determining the UV absorption of the products. The N-sulfonylated products exhibit an absorption maximum at 360 nm which the O-sulfonylated products do not have.

If exclusively 1-methyl-1H-imidazole is used in an amount of less than one equivalent, based on the 3-triazinyloxindole used, a reduced yield is to be expected.

However, it was now surprisingly found that a selective N-sulfonylation of the starting material is even possible when using a mixture which consists of a 1-alkyl-1H-imidazole and either a tertiary cyclic amine base such as diazabicyclo[2.2.2] octane (DABCO), methylmorpholine, 1-ethylmorpholine, N,N-dimethylpiperazine or 1,2-bis(dimethylamino)ethane or a substituted pyridine base such as 5-ethyl-2-methylpyridine, and in which less than one equivalent of 1-methyl-1H-imidazole, based on the 3-triazinyloxindole used, is present (Example 1, variant C).

It is also within the scope of the invention that, besides the imidazole bases substituted in the 1 position, a mixture of different base types is used, in which case one base type is an imidazole base substituted in the 1 position. Preference is given to a base mixture which comprises at least one
 tertiary amine base, or
 substituted pyridine base, and
additionally at least one of the following imidazole bases substituted in the 1 position
 1-(C$_1$-C$_6$)alkyl-1H-imidazole,
 1-cycloalkyl-1H-imidazole,
 1-benzyl-1H-imidazole,
 1-aryl-1H-imidazole, or
 1-hetaryl-1H-imidazole.

The tertiary amine bases used are preferably diazabicyclo [2.2.2]octane (DABCO), 1-methylmorpholine, 1-ethylmorpholine, N,N-dimethylpiperazine or 1,2-bis(dimethylamino) ethane.

As substituted pyridine base in mixtures with one or more 1-alkyl-1H-imidazoles, preference is given to using 5-ethyl-2-methylpyridine or 3-methylpyridine or a mixture of the two.

One important aspect relates to the choice of solvent in which the reaction is carried out. The reaction can be carried out in
 a polar, or
 a nonpolar solvent, or in
 a mixture of a polar or nonpolar solvent.
 Nonpolar solvents which can be used are
 aromatics, in particular toluene, xylene or chlorobenzene.
 Polar organic solvents which can be used are
 haloalkanes, in particular dichloromethane or dichloroethane; or
 ketones, in particular butanone, 2-methylbutanone;
 nitriles, in particular acetonitrile, butyronitrile, isobutylnitrile;
 ethers, in particular dioxane, 2-methyltetrahydrofuran, tert-butyl methyl ether, cyclopropyl methyl ether, dimethoxyethane or tetrahydrofuran; or
 esters, in particular ethyl acetate, n-butyl acetate or isopropyl acetate.

The specified polar solvents can either be used on their own or in mixtures with other solvents, preferably with other polar organic solvents.

Particular preference is given to carrying out the process with dichloromethane, 2-methyltetrahydrofuran or ethyl acetate as solvent or with a mixture which comprises at least one of the aforementioned particularly preferred solvents.

The process according to the invention for the preparation of compounds of the formula (3) is based on the fact that the 3-triazinyloxindole (1 equivalent) in a suitable solvent is reacted with the sulfonyl compound and an imidazole base, or a mixture comprising an imidazole base. Here, the sulfonyl compound is used in an equimolar amount or in excess (1.0 to 6 equivalents), preferably 1.2 to 2 equivalents). The base, either alone or as a mixture of two or more bases, is likewise used in an equimolar amount or in excess (1.0 to 7 equivalents, preferably 1.4 to 2.5 equivalents).

The addition of the reactants can take place in one or more portions over a period of up to 24 hours, preferably up to 6 hours, in particular 0.05 to 6 hours.

The reaction temperature of the sulfonylation is in the range from −100° C. to 50° C., preferably in the range from −20° C. to +10° C.

The reaction can optionally be carried out under pressure.

For good product yields, it is advantageous if firstly the 3-triazinyloxindole with the base (total amount or part amount) is introduced as initial charge in a suitable solvent and then the sulfonyl compound and optionally a further amount of the same base or of another base or of a mixture of different bases is added in one or more portions.

An addition variant involves introducing 3-triazinyloxindole and sulfonyl compound as initial charge in a suitable solvent and then adding the base or a mixture of different bases in one or more portions. Alternatively, the 3-triazinyloxindole can also be added in one or more portions to the initial charge of sulfonyl compound and the base.

It is within the scope of the invention that the 3-triazinyloxindole is added as salt to the reaction mixture. In this case, optionally less base can be used.

All reactants can be added to the reaction mixture either in pure form or premixed with one another or dissolved or suspended in a solvent or a solvent mixture. It is possible that in the course of the reaction further solvent is added in order to facilitate a better mixing of the reactants.

Depending on the reaction conditions used, the after-stirring time following the addition of all of the reactants is in the region of up to 96 hours, preferably 0.05 to 24 hours.

An after-stirring time is advantageous particularly when $R^3$=H since particularly in this case, during the sulfonylation reaction, the O-sulfonylated product can also at least partially be formed, which in turn, as explained above, under the influence of an imidazole base, is converted to the desired N-sulfonylated product of the formula (3), and/or can react further.

Work-up and isolation of the desired product of the formula (3) can take place in various ways and is dependent for example on the choice of solvent or is dependent on whether the product is a solid or a liquid.

The reaction mixture which comprises a solid product of the formula (3) or (3-1) is filtered. The solid product obtained in this way can be washed with suitable solvents and/or aqueous acids.

Moreover, it is provided that to the reaction mixture which comprises product of the formula (3), another, higher-boiling solvent is added in which the product has poorer solubility, and the lower-boiling solvent is completely or partially distilled off. The product, which is present as a solid, is then filtered off and can be washed with suitable solvents and/or aqueous acids.

Moreover, it is within the scope of the invention that the product obtained after filtration and optional washing is extracted from a suitable solvent or a mixture of two or more solvents by stirring in order to obtain a higher purity.

Furthermore, it is provided that the products of the formula (3), or (3-1) or salts thereof (3-1a) present in the reaction mixture are further reacted without isolation to give consecutive products.

The invention also provides N-sulfonyl-substituted 3-triazinyloxindoles of the formula (3-1) or salts thereof (3-1a), irrespective of the nature of the preparation of these compounds.

Thus included are N-sulfonyl-substituted 3-triazinyloxindoles of the formula (3-1)

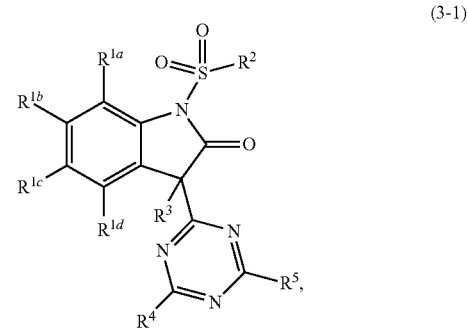

(3-1)

and salts thereof (3-1a)

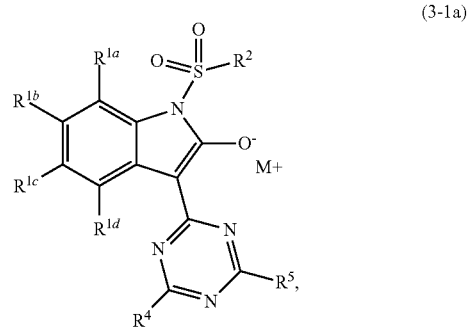

(3-1a)

in which, in each case, $R^{1a}$ to $R^{1d}$, independently of one another, are selected from the group consisting of hydrogen, fluorine, chlorine, bromine, iodine, and also of ($C_1$-$C_6$)-alkyl, where the alkyl radical is branched or unbranched and is unsubstituted or is substituted by one or more substituents selected from the group consisting of fluorine, chlorine, ($C_1$-$C_4$)-alkoxy or ($C_3$-$C_7$)-cycloalkyl, ($C_3$-$C_7$)-cycloalkyl, where the cycloalkyl radical is unsubstituted or is substituted by one or more substituents selected from the group consisting of fluorine, chlorine, ($C_1$-$C_4$)-alkyl or ($C_3$-$C_7$)-cycloalkyl or ($C_1$-$C_4$)-alkoxy, ($C_1$-$C_6$)-alkoxy, where the alkoxy radical is branched or unbranched and is unsubstituted or is substituted by one or more substituents selected from the group consisting of fluorine, chlorine, ($C_1$-$C_4$)-alkoxy or ($C_3$-$C_7$)-cycloalkyl, ($C_3$-$C_7$)-cycloalkoxy, where the cycloalkoxy radical is unsubstituted or is substituted by one or more substituents selected from the group consisting of fluorine, chlorine, ($C_1$-$C_4$)-alkyl or ($C_1$-$C_4$)-alkoxy, ($C_1$-$C_6$)-alkylthio, where the alkylthio radical is branched or unbranched and is unsubstituted or is substituted by one or more substituents selected from the group consisting of fluorine, chlorine, ($C_1$-$C_4$)-alkyl or ($C_1$-$C_4$)-alkoxy, ($C_3$-$C_7$)-cycloalkylthio, where the cycloalkylthio radical is unsubstituted or is substituted by one or more substituents selected from the group consisting of fluorine, chlorine, ($C_1$-$C_4$)-alkyl or ($C_1$-$C_4$)-alkoxy, and phenyl or 1-naphthyl or 2-naphthyl or a five- or six-membered heteroaromatic ring having 1 to 2 heteroatoms, where the heteroatoms, independently of one another, are selected from the group consisting of O or N, and where the aryl or heteroaryl radical is unsubstituted or is substituted by one or more substituents selected from the group consisting of fluorine, chlorine, bromine, iodine, $(C_1\text{-}C_4)$-alkyl, $(C_1\text{-}C_4)$-alkoxy or $(C_3\text{-}C_7)$-cycloalkyl or $(C_1\text{-}C_4)$-alkylthio, and $R^2$ is methyl, where the methyl is completely or partially substituted with fluorine, or $(C_3\text{-}C_7)$-cycloalkyl, where the cycloalkyl radical is completely or partially substituted with fluorine, $R^3$ is hydrogen, or $(C_1\text{-}C_6)$-alkyl, where the alkyl radical is branched or unbranched and is unsubstituted or is substituted by one or more substituents selected from the group consisting of fluorine, chlorine, $(C_1\text{-}C_4)$-alkoxy or $(C_3\text{-}C_7)$-cycloalkyl, $(C_1\text{-}C_6)$-alkylthio, where the alkylthio radical is unsubstituted or is substituted by one or more substituents selected from the group consisting of fluorine, chlorine, $(C_1\text{-}C_4)$-alkyl or $(C_1\text{-}C_4)$-alkoxy, $R^4$ and $R^5$, independently of one another, are in each case hydrogen, $(C_1\text{-}C_6)$-alkyl, where the alkyl radical is unsubstituted or is substituted by one or more substituents selected from the group consisting of fluorine, chlorine, $(C_1\text{-}C_4)$-alkoxy or $(C_3\text{-}C_7)$-cycloalkyl, $(C_1\text{-}C_6)$-alkoxy, where the alkoxy radical is branched or unbranched and is unsubstituted or is substituted by one or more substituents selected from the group consisting of fluorine, chlorine, $(C_1\text{-}C_4)$-alkoxy or $(C_3\text{-}C_7)$-cycloalkyl, where, in the salts of the formula (3-1a), M is Li, Na, K, Cs, Ba, Mg, Ca, Zn or $N(R^c)_4$, where $R^c$=H or $C_1\text{-}C_6$ alkyl, and where the number of counterions $M^+$ is determined by the particular charge, such that an overall neutral compound of the formula (3-1a) is formed.

If applicable, all stereoisomers, rotamers, tautomers and polymorphic forms are also included by the formulae (3-1) and (3-1a).

Particular preference is given to compounds of the formula (3-1) or salts of the formula (3-1a), where $R^{1a}$ to $R^{1d}$, independently of one another, are selected from the group consisting of hydrogen, fluorine, chlorine, and also from $(C_1\text{-}C_6)$-alkyl, where the alkyl radical is branched or unbranched, or $(C_1\text{-}C_6)$-alkoxy, where the alkoxy radical is branched or unbranched, and $R^2$ is difluoromethyl or trifluoromethyl, $R^3$ is hydrogen, $R^4$ and $R^5$, independently of one another, are in each case $(C_1\text{-}C_4)$-alkyl, where the alkyl radical is branched or unbranched, $(C_1\text{-}C_4)$-alkoxy, where the alkoxy radical is branched or unbranched, where, in the salts of the formula (3-1a), M is Na and K.

Very particular preference is given to compounds of the formula (3-1) or salts thereof of the formula (3-1a), where $R^{1a}$ to $R^{1d}$, independently of one another, are selected from the group consisting of hydrogen, fluorine, chlorine, methoxy, and $R^2$ is difluoromethyl, $R^3$ is hydrogen, and $R^4$ and $R^5$, independently of one another, are in each case methoxy.

Most preference is given to compounds of the formula (3-1) or salts thereof of the formula (3-1a), where $R^{1a}$ to $R^{1d}$, independently of one another, are selected from the group consisting of hydrogen and fluorine.

The invention also provides the use of the compounds of the formulae (3) or (3-1) or salts thereof (3-1a) prepared according to the invention as active ingredients in pharmacy or in agriculture, and also the use of the specified compounds for producing active ingredients from agriculture or for producing intermediates for the production of fine chemicals and active ingredients for agriculture.

Particular preference is given to the use as fungicide or herbicide, and/or the production of fungicides and herbicides, and/or the use of the specified compounds as intermediates for producing fungicides and herbicides.

The use of the specified compounds as herbicide, and/or the production of herbicides is very particularly preferred.

N-sulfonyl-substituted 3-triazinyloxindoles of the formulae (3-1) and (3-1a) and also the other N-sulfonyl-substituted 3-heteroaryloxindoles of the formula (3) prepared by the process according to the invention are suitable as intermediates for producing fine chemicals and active ingredients for agriculture.

From them, it is possible to produce N-alkyl-N-[2-(1,3,5-triazin-2-ylcarbonyl)phenyl]alkanesulfonamides of the formula (4-1)-see scheme 4 below-, whose herbicidal activity (see WO 2007/031208 A2) and fungicidal activity (see WO 2006/008159 A1) is shown in the two cited laid-open specifications.

Compounds of the formula (3) are N-sulfonyl-substituted 3-triazinyloxindoles.

In scheme 4 below, N-sulfonyl-substituted 3-triazinyloxindoles are denoted by the formula (3-1).

Scheme 4 shows a new multistage synthesis process, according to which, starting from a 3-(alkylsulfanyl)-1,3-dihydro-2H-indol-2-one of the formula (7-1) in an overall five-stage reaction, an N-alkyl-N-[2-(1,3,5-triazin-2-ylcarbonyl)phenyl]alkanesulfonamide of the formula (4-1) can be prepared, whose herbicidal activity (see WO 2007/031208 A2) and fungicidal activity (see WO 2006/008159 A1) has already been known for a relatively long time.

Scheme 4: Multistage process for the preparation of N-alkyl-N-[2-(1,3,5-triazin-2-ylcarbonyl)phenyl]alkanesulfonamides (4-1), in particular herbicidal ones, suitable for crop protection

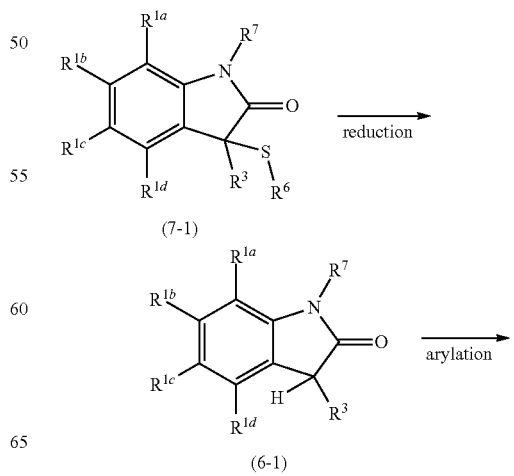

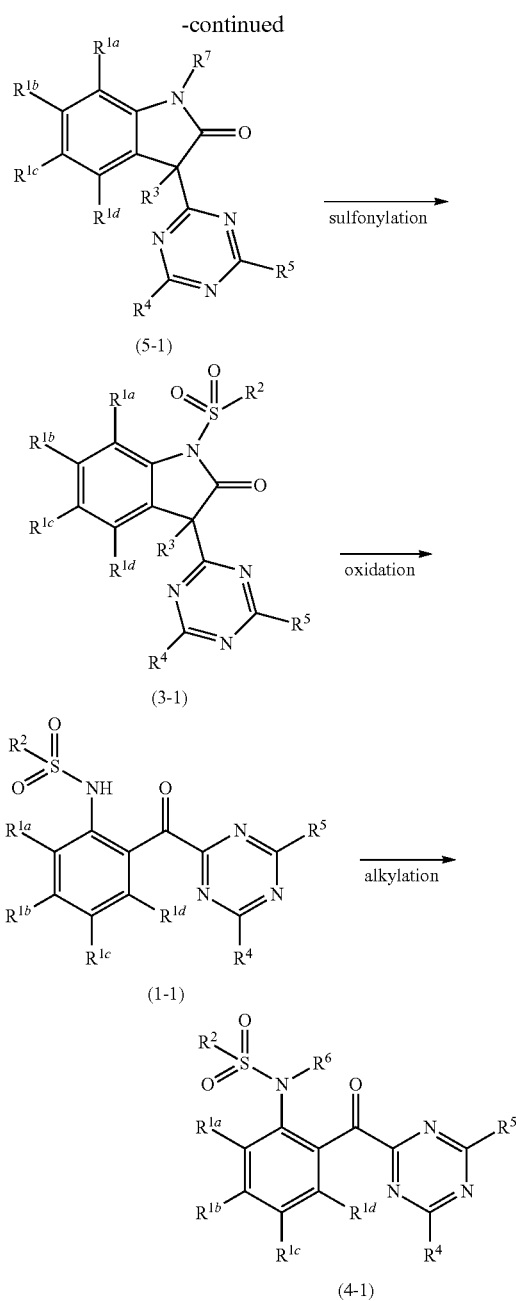

(5-1)

(3-1)

(1-1)

(4-1)

The multistage process according to scheme 4 for the preparation of N-alkyl-N-[2-(1,3,5-triazin-2-ylcarbonyl) phenyl]alkanesulfonamides (4-1) consists of the following part steps:

Reduction of substituted or unsubstituted 3-(alkylsulfanyl)-1,3-dihydro-2H-indol-2-ones (7-1) to give substituted or unsubstituted 1,3-dihydro-2H-indol-2-ones (6-1). This process is possible on an industrial scale and is described in the patent application with the application number EP 10162381.7.

Arylation of substituted or unsubstituted 1,3-dihydro-2H-indol-2-ones (6-1) to give triazinyl-substituted oxindoles (5-1). This process is possible on an industrial scale and is described in the patent application with the application number EP 10196205.8.

Sulfonylation of triazinyl-substituted oxindoles (5-1) to give N-sulfonyl-substituted 3-triazinyloxindoles (3-1) according to the present sulfonylation process according to the invention.

Oxidative ring-opening of N-sulfonyl-substituted 3-triazinyloxindoles (3-1) to give 2-(triazinylcarbonyl)sulfonanilides (1-1). This process is possible on an industrial scale and is described in the patent application DE 102011086382.6.

Alkylation of 2-(triazinylcarbonyl)sulfonanilides (1-1) to give N-alkyl-N-[2-(1,3,5-triazin-2-ylcarbonyl)phenyl] alkanesulfonamides (4-1). This process is described in the patent application with the application number WO 2006/008159 A1.

Compared with the previously known processes for the preparation of N-alkyl-N-[2-(1,3,5-triazin-2-ylcarbonyl) phenyl]alkanesulfonamides (4-1) and 2-(triazinylcarbonyl) sulfonanilides (1-1), the multistage process shown in scheme 4 is notable for the fact that oxindole compounds are used as starting materials and/or as intermediates. This has the advantage that the process can be carried out on an industrial scale, in contrast to the previously known processes, and at the same time high yields can be attained.

The way in which the process summarized in scheme 4 is carried out is disclosed in detail below. The reduction, which refers in scheme 4 to the first reaction step of the overall five-stage process, has been treated below as independent preliminary stage B). The process A) described in detail below thus involves only the steps of arylation, sulfonylation, oxidation and alkylation.

A) Process for the preparation of N-alkyl-N-[2-(1,3,5-triazin-2-ylcarbonyl)-phenyl]alkanesulfonamides of the formula (4-1)

(4-1)

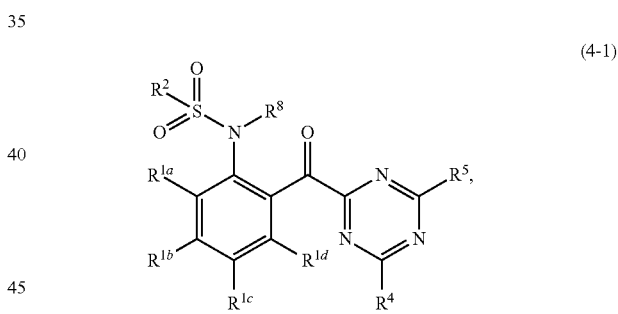

in which
$R^{1a}$ to $R^{1d}$, independently of one another, are selected from the group consisting of hydrogen, fluorine, chlorine, bromine, iodine, and also of
($C_1$-$C_6$)-alkyl, where the alkyl radical is unsubstituted or is substituted by one or more substituents selected from the group consisting of fluorine, chlorine, ($C_1$-$C_4$)-alkoxy or ($C_3$-$C_7$)-cycloalkyl,
($C_3$-$C_7$)-cycloalkyl, where the cycloalkyl radical is unsubstituted or is substituted by one or more substituents selected from the group consisting of fluorine, chlorine, ($C_1$-$C_4$)-alkyl or ($C_3$-$C_7$)-cycloalkyl or ($C_1$-$C_4$)-alkoxy,
($C_1$-$C_6$)-alkoxy, where the alkoxy radical is unsubstituted or is substituted by one or more substituents selected from the group consisting of fluorine, chlorine, ($C_1$-$C_4$)-alkoxy or ($C_3$-$C_7$)-cycloalkyl,
($C_3$-$C_7$)-cycloalkoxy, where the cycloalkoxy radical is unsubstituted or is substituted by one or more substituents selected from the group consisting of fluorine, chlorine, ($C_1$-$C_4$)-alkyl or ($C_1$-$C_4$)-alkoxy, ($C_1$-$C_6$)-alkylthio, where the alkylthio radical is unsubstituted or is substituted by one or more substituents selected from the group consisting of fluorine, chlorine, ($C_1$-$C_4$)-alkyl or ($C_1$-$C_4$)-alkoxy, ($C_3$-$C_7$)-cycloalkylthio, where the cycloalkylthio radical is unsubstituted or is substituted by one or more substituents selected from the group consisting of fluorine, chlorine, ($C_1$-$C_4$)-alkyl or ($C_1$-$C_4$)-alkoxy, and phenyl or 1-naphthyl or 2-naphthyl or a five- or six-membered heteroaromatic ring having 1 to 2 heteroatoms, where the heteroatoms, independently of one another, are selected from the group consisting of O or N, and where the aryl or heteroaryl radical is unsubstituted or is substituted by one or more substituents selected from the group consisting of fluorine, chlorine, bromine, iodine, ($C_1$-$C_4$)-alkyl, ($C_1$-$C_4$)-alkoxy or ($C_3$-$C_7$)-cycloalkyl or ($C_1$-$C_4$)-alkylthio, and $R^2$ is ($C_1$-$C_6$)-alkyl, where the alkyl radical is unsubstituted or is completely or partially substituted with fluorine, or ($C_3$-$C_7$)-cycloalkyl, where the cycloalkyl radical is unsubstituted or is completely or partially substituted with fluorine, $R^4$ and $R^5$, independently of one another, are in each case hydrogen, ($C_1$-$C_6$)-alkyl, where the alkyl radical is unsubstituted or is substituted by one or more substituents selected from the group consisting of fluorine, chlorine, ($C_1$-$C_4$)-alkoxy or ($C_3$-$C_7$)-cycloalkyl, ($C_1$-$C_6$)-alkoxy, where the alkoxy radical is branched or unbranched and is unsubstituted or is substituted by one or more substituents selected from the group consisting of fluorine, chlorine, ($C_1$-$C_4$)-alkoxy or ($C_3$-$C_7$)-cycloalkyl, and $R^8$ is ($C_1$-$C_6$)-alkyl, where the alkyl radical is unsubstituted or is completely or partially substituted with fluorine, ($C_1$-$C_6$)-cycloalkyl, ($C_1$-$C_6$)-alkenyl or ($C_1$-$C_6$)-alkoxyalkyl, where each of the specified radicals is unsubstituted or is completely or partially substituted with fluorine, where a 1,3-dihydro-2H-indol-2-one of the formula (6-1)

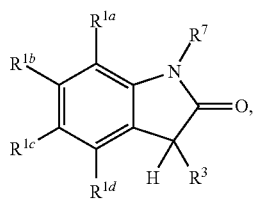

(6-1)

in which $R^{1a}$ to $R^{1d}$ are as defined for formula (4-1), $R^3$ is hydrogen, and $R^7$ is hydrogen, is reacted in a first step by arylation to give a triazinyl-substituted oxindole of the formula (5-1)

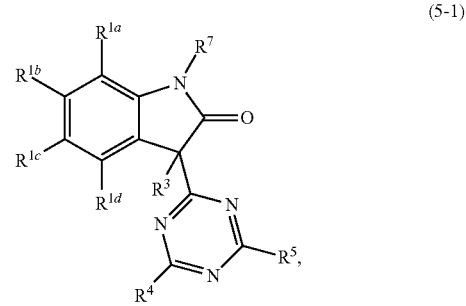

(5-1)

in which $R^{1a}$ to $R^{1d}$ and $R^4$ and $R^5$ are as defined for formula (4-1) and $R^3$ and $R^7$ are as defined for formula (6-1), and the arylation products of the formula (5-1) are reacted in a second step by sulfonylation to give N-sulfonyl-substituted 3-triazinyloxindoles of the formula (3-1)

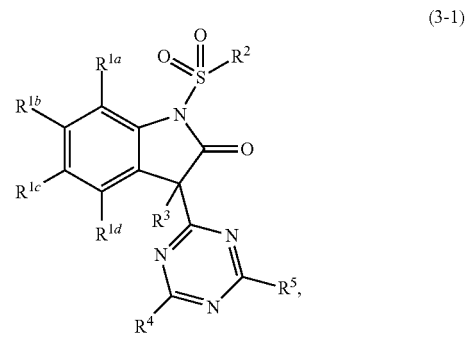

(3-1)

in which $R^{1a}$ to $R^{1d}$, $R^2$ and $R^4$ and $R^5$ are as defined in formula (4-1) and $R^3$ is as defined for formula (6-1), and the sulfonylation products of the formula (3-1) are reacted in a third step by oxidative ring-opening to give a 2-(triazinylcarbonyl)sulfonanilide of the formula (1-1)

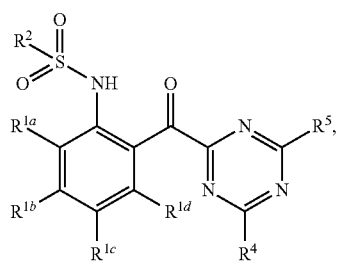

(1-1)

in which $R^{1a}$ to $R^{1d}$, $R^2$ and also $R^4$ and $R^5$ are as defined for formula (4-1), and the oxidation products of the formula (I-1) are reacted in a fourth step by
alkylation to give an N-alkyl-N-[2-(1,3,5-triazin-2-ylcarbonyl)phenyl]alkanesulfonamide of the formula (4-1)

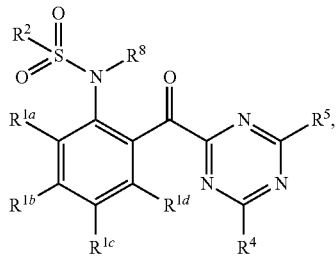

(4-1)

in which
R$^{1a}$ to R$^{1d}$, R$^2$, R$^4$, R$^5$ and R$^8$ are as defined above for formula (4-1),
where the alkylating reagent used is
X—R$^8$, where X is chlorine, bromine or iodine, and R$^8$ is as defined above for formula (4-1), or
(R$^8$)$_2$SO$_4$, in which R$^8$ is as defined above for formula (4-1).

The sulfonylation takes place in accordance with the teaching of the present invention, i.e. in the presence of
an imidazole base substituted in the 1 position, or
a base mixture which comprises at least one imidazole base substituted in the 1 position.

Particularly preferred imidazole bases are 1-methyl-1H-imidazole, 1-butyl-1H-imidazole or 1-benzyl-1H-imidazole, which can be used individually or in a mixture, with the use of 1-methyl-1H-imidazole being very particularly preferred.

B) Process for the preparation of N-alkyl-N-[2-(1,3,5-triazin-2-ylcarbonyl)phenyl]-alkanesulfonamides of the formula (4-1), where the compounds of the formula (6-1) used as starting material are prepared in a preceding process step in which, proceeding from a 3-(alkylsulfanyl)-1,3-dihydro-2H-indol-2-one of the formula (7-1),

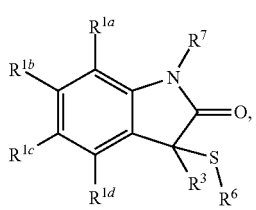

(7-1)

in which
R$^{1a}$ to R$^{1d}$ are as defined for formula (4-1),
R$^3$ is hydrogen,
R$^7$ is hydrogen, and
R$^6$ is an unsubstituted or substituted (C$_1$-C$_{14}$)-alkyl, (C$_3$-C$_7$)-cycloalkyl, benzyl or a CH$_2$—C(O)O—(C$_1$-C$_6$)-alkyl, is converted by
reduction to give a 1,3-dihydro-2H-indol-2-one (6-1)

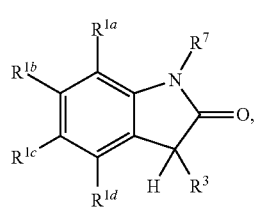

(6-1)

in which
R$^{1a}$ to R$^{1d}$, R$^3$ and R$^7$ are as defined for formula (7-1).
When carrying out the reduction,
a) a compound of the formula (7-1) is dissolved or suspended in a polar solvent,
b) a sulfur-containing salt is added to the solution or to the suspension, and
c) the reaction mixture is heated under reflux at a temperature which corresponds at most to the boiling temperature of the polar solvent.

The particularly preferred sulfur-containing salts are sodium salts, selected from the group consisting of sodium bisulfite, sodium sulfite, sodium thionite, sodium dithionite and sodium thiosulfate.

The herbicidal effect (see WO 2007/031208 A2) and fungicidal effect (see WO 2006/008159 A1) of N-alkyl-N-[2-(1,3,5-triazin-2-ylcarbonyl)phenyl]alkanesulfonamides of the formula (4-1) has, as already mentioned, been known for a relatively long time.

Consequently, scheme 4 and the way in which processes A) and B) are carried out demonstrate that heteroaryl-substituted oxindoles of the formula (3), and triazinyl-substituted oxindoles of the formula (3-1) or salts thereof (3-1a) are suitable as intermediates for producing crop protection compositions, in particular herbicides and fungicides.

The use of compounds of the formulae (3) or (3-1) or salts thereof (3-1a) as intermediates for producing N-[2-(1,3,5-triazin-2-ylcarbonyl)phenyl]alkylsulfonamides is most preferred.

The examples below illustrate the invention in more detail, but without limiting its subject matter to these examples.

In the examples below, quantitative data is based on the weight, unless specifically defined otherwise (in the description, % by wt.=percent by weight was used analogously for this). For measurement units, physical parameters and the like, customary abbreviations are used, for example h=hour(s), m.p.=melting point, l=liter, ml=milliliter, g=gram, min=minute(s), in vacuo="in a vacuum"=under reduced pressure, of theory=percent yield according to the theory, RT=room temperature, eq.=equivalents.

The coupling patterns in the NMR spectra are described how they appear.

Unless stated otherwise, fractions in the HPLC analysis are given in relative area percentages.

Percentages in the LCMS analysis refer to the relative fraction of the respective component in the chromatogram.

Example 1

Preparation of 1-[(difluoromethyl)sulfonyl]-3-(4,6-dimethoxy-1,3,5-triazin-2-yl)-7-fluoro-1,3-dihydro-2H-indol-2-one

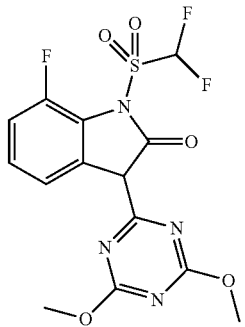 [SMILES: COc1nc(OC)nc(C2C(=O)N(S(=O)(=O)C(F)F)c3c(F)cccc32)n1]

Variant A:

3-(4,6-Dimethoxy-1,3,5-triazin-2-yl)-7-fluoro-1,3-dihydro-2H-indol-2-one (95.7 g) and 1-methyl-1H-imidazole (53.1 g) are introduced as initial charge in 1120 ml of ethyl acetate and cooled to 0° C. under nitrogen. With vigorous stirring, difluoromethanesulfonyl chloride (73.7 g) is added dropwise at 0° C. to 5° C. over the course of 30 minutes and the mixture is after-stirred for 3.5 hours. Further difluoromethanesulfonyl chloride (4.9 g) is added to the reaction mixture, which is stirred for 1.5 hours. The reaction mixture is admixed with 500 ml of water and vigorously mixed. The organic solvent is largely distilled off in vacuo and the residue is filtered. The solid product is washed twice with in each case 250 ml of water, extracted from 400 ml of ethyl acetate/heptane (1:1) by stirring, filtered off and washed with 100 ml of ethyl acetate/heptane (1:1). This gives the title compound as a solid in a purity of 96% against standard (123.1 g, 91% of theory). The UV absorption (maximum at 360 nm) verifies the N-sulfonylation of the product.

LC-MS: M+H=405 (95%).

1H-NMR (400 MHz, CDCl$_3$): δ (ppm)=12.6 (s, broad, 1H), 7.83 (d, 1H), 7.20 (dt, 1H), 6.93 (dd, 1H), 6.70 (t, 1H), 4.21 (s, 3H), 4.16 (s, 3H).

Variant B:

3-(4,6-Dimethoxy-1,3,5-triazin-2-yl)-7-fluoro-1,3-dihydro-2H-indol-2-one (100 g) and 1-methyl-1H-imidazole (44.8 g) are introduced as initial charge in 670 ml of dichloromethane and cooled to −10° C. under nitrogen. With vigorous stirring, difluoromethanesulfonyl chloride (72.6 g) is added dropwise at −12° C. to −3° C. over the course of 35 minutes and the mixture is after-stirred for 4.5 hours at −10° C. to −5° C. AN HPLC check after one hour and 3 hours shows the presence of the O-sulfonylated starting material produced as intermediate which, at the end of the reaction, has been virtually completely converted into the desired product. The reaction mixture is admixed with 500 ml of water and vigorously mixed. The organic solvent is largely distilled off in vacuo and the residue is filtered. The solid product is washed twice with in each case 100 ml of 5% strength hydrochloric acid and twice with in each case 100 ml of water and dried in a vacuum drying cabinet. This gives the title compound as a solid in a purity of 93% against standard (136 g, 93% of theory). The NMR signals of the product agree with the signals of the product obtained according to variant A.

Variant C:

3-(4,6-Dimethoxy-1,3,5-triazin-2-yl)-7-fluoro-1,3-dihydro-2H-indol-2-one (10 g; 33 mmol) is introduced as initial charge in 40 ml of dichloromethane and cooled to −20° C. 1-Methyl-1H-imidazole (0.84 g; 10 mmol) and 4-ethylmorpholine (5.5 g, 47 mmol) are added and the reaction mixture is briefly stirred. With vigorous stirring, difluoromethanesulfonyl chloride (6.2 g) is added dropwise at −20° C. to −10° C. and the mixture is after-stirred for 3 hours at −20° C. to −10° C. It is admixed with 50 ml of dichloromethane and after-stirred for one hour. Difluoromethanesulfonyl chloride (0.5 g) is added and the mixture is after-stirred for one hour. The reaction mixture is heated to room temperature, transferred to a stirring-out flask and admixed with 100 ml of water. The organic solvent is largely distilled off in vacuo and the residue is filtered. The solid product is washed with in each case 50 ml of 5% strength hydrochloric acid, water and 2-propanol and dried in a vacuum drying cabinet. This gives the title compound as a solid in an HPLC purity of 98.8% (13.3 g, 97% of theory). The NMR signals of the product agree with the signals of the product obtained according to variant A.

Variant D (=Comparative Example 1D):

3-(4,6-Dimethoxy-1,3,5-triazin-2-yl)-7-fluoro-1,3-dihydro-2H-indol-2-one (3.0 g) is introduced as initial charge in 60 ml of tetrahydrofuran and cooled to 0° C., and sodium hydride (0.52 g, 60% in mineral oil) is added. The reaction mixture is stirred for one hour, difluoromethanesulfonyl chloride (1.7 g) is added dropwise at 0° C. and the mixture is after-stirred for 12 hours at 0° C. HPLC analysis detects starting material (72%), the desired product (8%) and further components.

Variant E (=Comparative Example 1E):

3-(4,6-Dimethoxy-1,3,5-triazin-2-yl)-7-fluoro-1,3-dihydro-2H-indol-2-one (3.0 g) is introduced as initial charge in 60 ml of tetrahydrofuran and cooled to −30° C., and potassium tert-butylate (1.26 g) is added. The reaction mixture is then warmed to 0° C. over the course of one hour, then cooled to −60° C., difluoromethanesulfonyl chloride (1.7 g) is added dropwise, and the mixture is slowly warmed to room temperature and after-stirred for 12 hours. HPLC analysis detects starting material (61%), the desired product (6%) and further components.

Variant F (=Comparative Example 1F):

3-(4,6-Dimethoxy-1,3,5-triazin-2-yl)-7-fluoro-1,3-dihydro-2H-indol-2-one (3.0 g) is introduced as initial charge in 30 ml of dichloromethane and cooled to −15° C., and triethylamine (1.86 g) is added. The reaction mixture is briefly stirred, difluoromethanesulfonyl chloride (2.2 g) is added dropwise, and the mixture is after-stirred for 3 hours at −15 to −10° C. The mixture stands for 15 hours at room temperature. HPLC analysis detects starting material (53%), the desired product (ca. 3%) and further components.

Variant G:

3-(4,6-Dimethoxy-1,3,5-triazin-2-yl)-7-fluoro-1,3-dihydro-2H-indol-2-one (3 g; 10 mmol) is introduced as initial charge in 50 ml of dichloromethane. 1-Methyl-1H-imidazole (0.17 g; 2.0 mmol) and 5-ethyl-2-methylpyridine (2.0 g, 16 mmol) are added, the reaction mixture is cooled to −10° C. and briefly stirred. With vigorous stirring, difluoromethanesulfonyl chloride (2.5 g, 16 mmol) is added dropwise at −20° C. to −5° C. and after-stirred for 7 hours at −20° C. to −5° C. The reaction mixture is warmed to room temperature, transferred to a stirring-out flask and admixed with 30 ml of water. The organic solvent is largely distilled off in vacuo and the residue is filtered. The solid product is washed with in each case 30 ml of 5% strength hydrochloric acid, water and 2-propanol and dried in a vacuum drying cabinet. This gives the title compound as a solid in an HPLC purity of 94% (3.7 g, 84% of theory).

Example 2

Preparation of 1-[(difluoromethyl)sulfonyl]-7-fluoro-3-(4-methoxy-6-methyl-1,3,5-triazin-2-yl)-1,3-dihydro-2H-indol-2-one

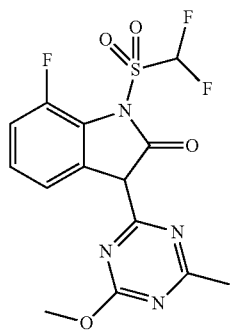 [SMILES: COc1nc(C)nc(C2C(=O)N(S(=O)(=O)C(F)F)c3c(F)cccc32)n1]

7-Fluoro-3-(4-methoxy-6-methyl-1,3,5-triazin-2-yl)-1,3-dihydro-2H-indol-2-one (1.20 g) and 1-methyl-1H-imidazole (0.97 g) are introduced as initial charge in 10 ml of dichloromethane and cooled to 0° C. under nitrogen. With stirring, difluoromethanesulfonyl chloride (1.21 g) is added in 2 portions and the mixture is warmed to room temperature. After 5 hours, 1-methyl-1H-imidazole (0.32 g) and difluoromethanesulfonyl chloride (0.61 g) are added and the mixture is stirred for 16 hours. After adding water and some hydrochloric acid, the solid is filtered off, washed with dichloromethane and water and dried. This gives the title compound as a solid in an HPLC purity of 91% (1.54 g, 92% of theory). The UV absorption (maximum at 360 nm) verifies the N-sulfonylation of the product.

LC-MS: M+H=389 (71%).

1H-NMR (400 MHz, DMSO-D$_6$): δ (ppm)=7.94 (d, 1H), 7.53 (t, 1H), 7.29 (dt, 1H), 7.03 (dd, 1H), 4.12 (s, 3H), 2.58 (s, 3H).

Example 3

Preparation of 1-[(difluoromethyl)sulfonyl]-3-(4,6-dimethoxy-1,3,5-triazin-2-yl)-1,3-dihydro-2H-indol-2-one

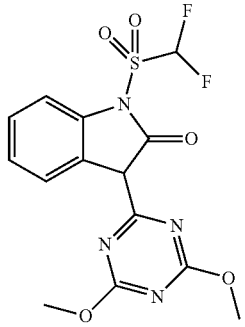 [SMILES: COc1nc(OC)nc(C2C(=O)N(S(=O)(=O)C(F)F)c3ccccc32)n1]

3-(4,6-Dimethoxy-1,3,5-triazin-2-yl)-1,3-dihydro-2H-indol-2-one (10 g) and 1-methyl-1H-imidazole (5.4 g) are introduced as initial charge in 100 ml of dichloromethane and cooled to −5° C. under nitrogen. With stirring, difluoromethanesulfonyl chloride (7.03 g) is added dropwise at −5° C. to 0° C. over the course of 20 minutes, and the mixture is after-stirred at this temperature for 2.5 hours. The reaction mixture is admixed with 50 ml of water and mixed thoroughly. The organic solvent is largely distilled off in vacuo and the residue is filtered. The solid product is washed with water and acetonitrile and dried in a vacuum drying cabinet. This gives the title compound as a solid in an HPLC purity of 93% (12.5 g, 92% of theory). The UV absorption (maximum at 360 nm) verifies the N-sulfonylation of the product.

LC-MS: M+H=387 (98%).

1H-NMR (400 MHz, CDCl$_3$): δ (ppm)=12.55 (s, broad, 1H), 7.98 (d, 1H), 7.76 (d, 1H), 7.23 (t, 1H), 7.16 (t, 1H), 6.68 (t, 1H), 4.22 (s, 3H), 4.15 (s, 3H).

Example 4

Preparation of 1-[(difluoromethyl)sulfonyl]-3-(4,6-dimethoxy-1,3,5-triazin-2-yl)-5-fluoro-1,3-dihydro-2H-indol-2-one

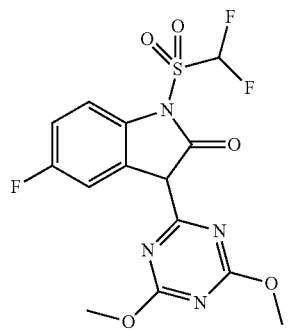 [SMILES: COc1nc(OC)nc(C2C(=O)N(S(=O)(=O)C(F)F)c3ccc(F)cc32)n1]

3-(4,6-Dimethoxy-1,3,5-triazin-2-yl)-5-fluoro-1,3-dihydro-2H-indol-2-one (50 g) and 1-methyl-1H-imidazole (30.5 g) are introduced as initial charge in 430 ml of dichloromethane and cooled to −10° C. under nitrogen. With stirring, a solution of difluoromethanesulfonyl chloride (41.8 g) in 70 ml of dichloromethane is added dropwise at −15° C. to −5° C. over the course of 30 minutes, and the mixture is after-stirred for 4 hours at −15° C. to 0° C. 1-Methyl-1H-imidazole (2.7 g) and difluoromethanesulfonyl chloride (4.9 g) are added to the reaction mixture and stirred for 2 hours at 0° C. With ice cooling, 300 ml of water are added to the reaction mixture, the mixture is after-stirred for 30 minutes and the organic solvent is largely distilled off in vacuo. The residue is filtered, the solid product is washed twice with 150 ml of water and twice with 40 ml of acetonitrile and dried. This gives the title compound as a solid in an HPLC purity of 96% (63.9 g, 95% of theory). The UV absorption (maximum at 360 nm) verifies the N-sulfonylation of the product.

LC-MS: M+H=405 (97%).

1H-NMR (400 MHz, CDCl$_3$): δ (ppm)=12.5 (s, broad, 1H), 7.63-7.72 (m, 2H), 6.85 (dt, 1H), 6.67 (t, 1H), 4.22 (s, 3H), 4.17 (s, 3H).

Example 5

Preparation of 3-(4,6-diethoxy-1,3,5-triazin-2-yl)-1-[(difluoromethyl)sulfonyl]-7-fluoro-1,3-dihydro-2H-indol-2-one

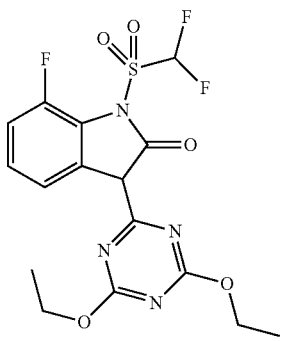 [SMILES: CCOc1nc(OCC)nc(C2C(=O)N(S(=O)(=O)C(F)F)c3c(F)cccc32)n1]

3-(4,6-Diethoxy-1,3,5-triazin-2-yl)-7-fluoro-1,3-dihydro-2H-indol-2-one (1.0 g) and 1-methyl-1H-imidazole (0.51 g) are introduced as initial charge in 10 ml of dichloromethane and cooled to 0° C. under nitrogen. With stirring, difluoromethanesulfonyl chloride (0.46 g) is added dropwise and the mixture is after-stirred for 2 hours at 0° C. to 6° C. After adding 1-methyl-1H-imidazole (0.25 g) and difluoromethanesulfonyl chloride (0.23 g), the mixture is stirred for 2 hours at 0° C. to 10° C. After adding 5 ml of water, the mixture is adjusted to pH 2 using 10% strength hydrochloric acid, the organic solvent is largely distilled off in vacuo, and the solid is filtered off, washed with water and heptane and dried. This gives the title compound as a solid in an HPLC purity of 93% (1.19 g, 83% of theory). The UV absorption (maximum at 360 nm) verifies the N-sulfonylation of the product.

LC-MS: M+H=433 (91%).

1H-NMR (400 MHz, DMSO-D$_6$): δ (ppm)=7.86 (dd, 1H), 7.52 (t, 1H), 7.22-7.31 (m, 1H), 7.00 (dd, 1H), 4.58 (q, 4H), 1.41 (t, 6H).

Example 6

Preparation of 1-[(difluoromethyl)sulfonyl]-3-(4,6-dimethoxy-1,3,5-triazin-2-yl)-5,7-difluoro-1,3-dihydro-2H-indol-2-one

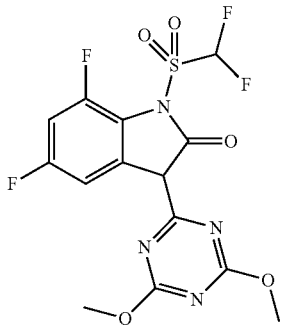 [SMILES: COc1nc(OC)nc(C2C(=O)N(S(=O)(=O)C(F)F)c3c(F)cc(F)cc32)n1]

3-(4,6-Dimethoxy-1,3,5-triazin-2-yl)-5,7-difluoro-1,3-dihydro-2H-indol-2-one (1.0 g), 1-methyl-1H-imidazole (0.74 g) and difluoromethanesulfonyl chloride (1.09 g) are reacted in 8 ml of dichloromethane analogously to Example 5. For the work-up, water is added and stirred, and the solid is filtered off, washed with dilute hydrochloric acid and water and dried. This gives the title compound as a solid in an HPLC purity of 97% (1.08 g, 82% of theory). The UV absorption (maximum at 360 nm) verifies the N-sulfonylation of the product.

LC-MS: M+H=423 (96%).

1H-NMR (400 MHz, DMSO-D$_6$): δ (ppm)=7.64 (dd, 1H), 7.51 (t, 1H), 7.00 (dt, 1H), 4.12 (s, 6H).

Example 7

Preparation of 1-[(difluoromethyl)sulfonyl]-3-(4,6-dimethoxy-1,3,5-triazin-2-yl)-5-methoxy-1,3-dihydro-2H-indol-2-one

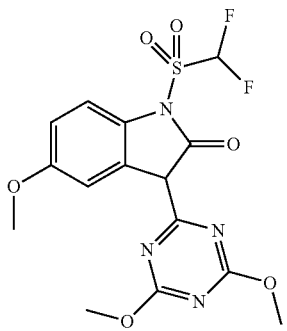

3-(4,6-Dimethoxy-1,3,5-triazin-2-yl)-5-methoxy-1,3-dihydro-2H-indol-2-one (1.0 g) and 1-methyl-1H-imidazole (0.51 g) are introduced as initial charge in 8 ml of dichloromethane and cooled to −10° C. under nitrogen. With stirring, difluoromethanesulfonyl chloride (0.66 g) is added dropwise in two portions and the mixture is stirred for 2.5 hours at −5 to −10° C. For the work-up, water is added and the mixture is stirred, and the solid is filtered off, washed with dilute hydrochloric acid and water and dried. This gives the title compound as a solid in an HPLC purity of 99% (0.91 g, 70% of theory). The UV absorption (maximum at 360 nm) verifies the N-sulfonylation of the product.

LC-MS: M+H=417 (100%).

1H-NMR (400 MHz, DMSO-D$_6$): δ (ppm)=7.61 (d, 1H), 7.46 (d, 1H), 7.44 (t, 1H), 6.71 (dd, 1H), 4.11 (s, 6H), 3.77 (s, 3H).

Example 8

Preparation of 1-[(difluoromethyl)sulfonyl]-3-(4,6-dimethoxy-1,3,5-triazin-2-yl)-7-methoxy-1,3-dihydro-2H-indol-2-one

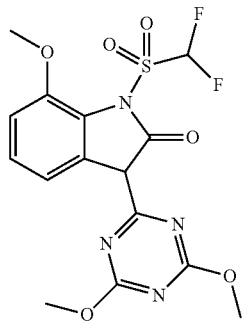 [SMILES: COc1nc(OC)nc(C2C(=O)N(S(=O)(=O)C(F)F)c3c(OC)cccc32)n1]

3-(4,6-Dimethoxy-1,3,5-triazin-2-yl)-7-methoxy-1,3-dihydro-2H-indol-2-one (1.0 g) and 1-methyl-1H-imidazole (0.47 g) are introduced as initial charge in 8 ml of dichloromethane and cooled to −15° C. with nitrogen. With stirring, difluoromethanesulfonyl chloride (0.62 g) is added dropwise in two portions and the mixture is heated to 10° C. in 2.5 hours. It is cooled to 0° C., 1-methyl-1H-imidazole (0.24 g) and difluoromethanesulfonyl chloride (0.35 g) are added, and the mixture is warmed to room temperature over the course of 3 hours, after-stirred for 4 hours and left to stand for 48 hours. For work-up, water is added and the mixture is stirred, and the solid is filtered off, washed with dilute hydrochloric acid and water and dried. This gives the title compound as a solid in an HPLC purity of 91% (0.52 g, 39% of theory). The UV absorption (maximum at 360 nm) verifies the N-sulfonylation of the product.

LC-MS: M+H=417 (87%).

1H-NMR (400 MHz, DMSO-$D_6$): δ (ppm)=7.68 (d, 1H), 7.46 (t, 1H), 7.23 (t, 1H), 6.90 (d, 1H), 4.11 (s, 6H), 3.88 (s, 3H).

Example 9

Preparation of 3-(4,6-dimethoxy-1,3,5-triazin-2-yl)-7-fluoro-1-[(trifluoromethyl)-sulfonyl]-1,3-dihydro-2H-indol-2-one

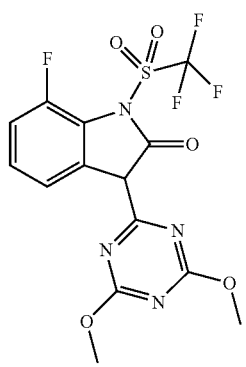 [SMILES: COc1nc(OC)nc(C2C(=O)N(S(=O)(=O)C(F)(F)F)c3c(F)cccc32)n1]

3-(4,6-Dimethoxy-1,3,5-triazin-2-yl)-7-fluoro-1,3-dihydro-2H-indol-2-one (1.0 g) and 1-methyl-1H-imidazole (1.09 g) are introduced as initial charge in 10 ml of dichloromethane and cooled to 0° C. under nitrogen. With stirring, trifluoromethanesulfonic anhydride (1.89 g) is added in 4 portions at an internal temperature of 0-10° C. The mixture is stirred for one hour at max. 15° C. The mixture is cooled again in an ice bath, water is added, hydrochloric acid is used to adjust the pH to 2 and the phases are separated. The organic phase is washed with water, dried and concentrated by evaporation. This gives the title compound as a solid in an HPLC purity of 68% (1.38 g, 67% of theory). The UV absorption (maximum at 360 nm) verifies the N-sulfonylation of the product.

LC-MS: M+H=423 (35%)

1H-NMR (400 MHz, DMSO-$D_6$): δ (ppm)=7.96 (d, 1H), 7.32 (dt, 1H), 7.03 (dd, 1H), 4.12 (s, 6H).

Example 10

Preparation of 3-(4,6-dimethoxy-1,3,5-triazin-2-yl)-7-fluoro-1H-indol-2-yl trifluoromethanesulfonate

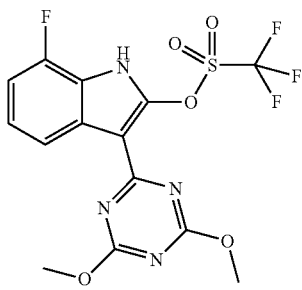 [SMILES: COc1nc(OC)nc(-c2c(OS(=O)(=O)C(F)(F)F)[nH]c3c(F)cccc23)n1]

3-(4,6-Dimethoxy-1,3,5-triazin-2-yl)-7-fluoro-1,3-dihydro-2H-indol-2-one (1.0 g) and 1,4-diazabicyclo[2.2.2]octane (0.82 g) are introduced as initial charge in 10 ml of dichloromethane and cooled to −10° C. under nitrogen. With stirring, trifluoromethanesulfonic anhydride (1.42 g) is added dropwise and the mixture is warmed to room temperature in 4.5 hours. The mixture stands for 15 hours. 1,4-Diazabicyclo[2.2.2]-octane (0.48 g) and trifluoromethanesulfonic anhydride (0.94 g) are added, and the mixture is stirred for 5 hours and adjusted to pH 1-2 with dilute hydrochloric acid. The solid is filtered off, washed with dichloromethane and water and dried. This gives the title compound as a solid in an HPLC purity of 88% (0.45 g, 28% of theory). The UV absorption (no maximum at 360 nm) verifies the O-sulfonylation of the product.

LC-MS: M+H=423 (52%)

1H-NMR (400 MHz, DMSO-$D_6$): δ (ppm)=11.4 (s, broad, 1H), 8.37 (d, 1H), 7.31 (dt, 1H), 7.24 (dd, 1H), 4.06 (s, 6H).

Example 11 (=Comparative Example 11)

Preparation of 3-phenyl-1H-indol-2-yl 4-methylbenzenesulfonate

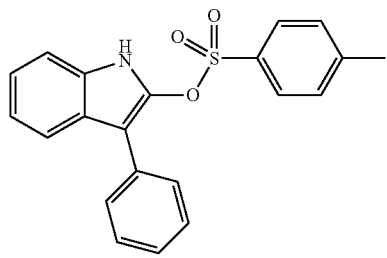 [SMILES: Cc1ccc(S(=O)(=O)Oc2[nH]c3ccccc3c2-c2ccccc2)cc1]

3-Phenyloxindole (1.15 g), 4-methylbenzenesulfonyl chloride (1.06 g) and sodium carbonate (0.41 g) are introduced as initial charge in 5.5 ml of water and 11 ml of acetone and heated to 80° C. with stirring in a preheated oil bath. After 20 minutes, 5 ml of acetone and 1 ml of water are then added and the mixture is heated for a further 30 minutes. The hot solution is filtered, and the solid is washed with 20 ml of water/acetone (1:1) and methanol and dried in vacuo. This gives 0.59 g of product in an HPLC purity of 98% (29% of theory). A structural elucidation by NMR verifies that it is the O-sulfonylated product. A further 0.67 g of product in an HPLC purity of 40% can be isolated from the filtrate (13% of theory).

LC-MS: M−H=362 (87%).

1H-NMR (400 MHz, DMSO-D$_6$): δ (ppm)=10.94 (s, 1H), 7.90-7.95 (m, 2H), 7.83 (d, 1H), 7.40-7.47 (m, 3H), 7.35 (t, 1H), 7.22-7.28 (m, 4H), 7.20 (t, 1H), 6.76 (d, 1H), 2.33 (s, 3H).

Example 12

Preparation of 1-[(difluoromethyl)sulfonyl]-3-(4,6-dimethoxy-1,3,5-triazin-2-yl)-7-fluoro-3-methyl-1,3-dihydro-2H-indol-2-one

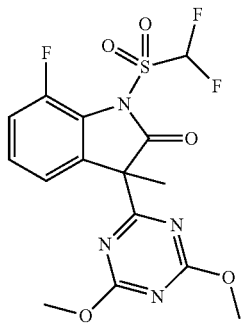 [SMILES: COc1nc(OC)nc(C2(C)C(=O)N(S(=O)(=O)C(F)F)c3c(F)cccc32)n1]

Step (a): 3-(4,6-Dimethoxy-1,3,5-triazin-2-yl)-7-fluoro-3-methyl-1,3-dihydro-2H-indol-2-one 3-(4,6-Dimethoxy-1,3,5-triazin-2-yl)-7-fluoro-1,3-dihydro-2H-indol-2-one (5.0 g) is introduced as initial charge in 225 ml of acetonitrile, sodium hydride (0.73 g, 60% in mineral oil) is added and the mixture is after-stirred until a thick suspension is formed. After adding iodomethane (7.0 g), the mixture is heated to 60° C. and stirred for 11 hours at 60° C. The organic solvent is largely distilled off in vacuo. 2-Propanol is added to the partially crystalline residue and the product is filtered off. This gives the intermediate as a solid in an HPLC purity of 93% (3.46 g, 64% of theory). The structure can be confirmed by NMR spectroscopy.

LC-MS: M+H=305 (89%).

1H-NMR (400 MHz, CDCl$_3$): δ (ppm)=8.91 (s, 1H), 6.95-7.03 (m, 2H), 6.91-6.95 (m, 1H), 4.02 (s, 6H), 1.90 (s, 3H).

Step (b): 1-[(Difluoromethyl)sulfonyl]-3-(4,6-dimethoxy-1,3,5-triazin-2-yl)-7-fluoro-3-methyl-1,3-dihydro-2H-indol-2-one Variant A:

3-(4,6-Dimethoxy-1,3,5-triazin-2-yl)-7-fluoro-3-methyl-1,3-dihydro-2H-indol-2-one (0.50 g) and 1-methyl-1H-imidazole (0.37 g) are introduced as initial charge in 5 ml of dichloromethane and cooled to −20° C. With stirring, difluoromethanesulfonyl chloride (0.58 g) is added dropwise and the mixture is slowly warmed to room temperature. The mixture is stirred for 3 hours at room temperature. HPLC analysis detects starting material (67%), the desired product (25%) and further components. The mixture is added to 10 ml of water, the phases are separated and the organic phase is concentrated by evaporation in vacuo. The residue is purified by chromatography and the product is separated off from the unreacted starting material. This gives the title compound in an HPLC purity of 86% (0.16 g, 22% of theory). By means of 2D-NMR, it is possible to confirm the structure as N-sulfonylated compound.

LC-MS: M+H=419 (85%).

1H-NMR (400 MHz, CDCl$_3$): δ (ppm)=7.10-7.25 (m, 3H), 6.67 (t, 1H), 4.02 (s, 6H), 1.94 (s, 3H).

Variant B:

3-(4,6-Dimethoxy-1,3,5-triazin-2-yl)-7-fluoro-3-methyl-1,3-dihydro-2H-indol-2-one (5.0 g) is suspended in 40 ml of dichloromethane. 1-Methyl-1H-imidazole (6.47 g) and 1,4-dimethylpiperazine (1.78 g) are added and the solution is stirred under nitrogen for 30 minutes at 45° C. The reaction mixture is cooled to 0° C., and a solution of difluoromethanesulfonyl chloride (11.9 g) in 20 ml of dichloromethane is added dropwise over the course of 30 minutes, during which the temperature is held at 0° C. The mixture is after-stirred for one hour at 0° C. After adding 200 ml of dichloromethane, the organic phase is washed with 200 ml of hydrochloric acid (2%) and with water. 100 ml of acetonitrile and a few drops of N,N-dimethylformamide are added to the organic phase, and washing is carried out several times alternately with 200 ml portions of an aqueous solution of potassium hydroxide (3%) and with water. The solvent is largely distilled off in vacuo. The residue is dissolved in 50 ml of toluene and washed three times with water. The solvent is distilled off in vacuo. This gives the title compound in an HPLC purity of 93% (4.06 g, 58% of theory).

The NMR signals of the product agree with the signals of the product obtained according to variant A.

Example 13 (=Comparative Example 13)

Preparation of 3-(4,6-dimethoxy-1,3,5-triazin-2-yl)-7-fluoro-1H-indol-2-yl 4-methylbenzenesulfonate

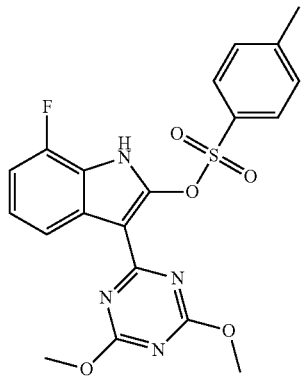 [SMILES: COc1nc(OC)nc(-c2c(OS(=O)(=O)c3ccc(C)cc3)[nH]c3c(F)cccc23)n1]

3-(4,6-Dimethoxy-1,3,5-triazin-2-yl)-7-fluoro-1,3-dihydro-2H-indol-2-one (1.15 g), 4-methylbenzenesulfonyl chloride (1.06 g) and sodium carbonate (0.41 g) are introduced as initial charge in 5.5 ml of water and 11 ml of acetone and, with stirring, heated to 80° C. in a preheated oil bath. After 45 minutes, the hot solution is filtered, and the solid is washed with 20 ml of water/acetone (1:1) and methanol and dried in vacuo. This gives 0.76 g of product in an HPLC purity of 97% (42% of theory). Structure elucidation by NMR verifies that it is the O-sulfonylated product. A further 0.41 g of product in an HPLC purity of 89% can be isolated from the filtrate (21% of theory).

LC-MS: M−H=443 (95%).

1H-NMR (400 MHz, DMSO-D$_6$): δ (ppm)=13.33 (s, 1H), 8.12 (d, 1H), 7.64 (d, 2H), 7.30 (d, 2H), 7.10-7.22 (m, 2H), 3.97 (s, 6H), 2.33 (s, 3H).

Example 14

Preparation of 7-chloro-1-[(difluoromethyl)sulfonyl]-3-(4,6-dimethoxy-1,3,5-triazin-2-yl)-1,3-dihydro-2H-indol-2-one

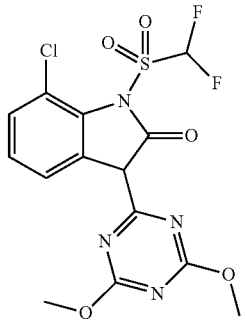 [SMILES: COc1nc(OC)nc(C2C(=O)N(S(=O)(=O)C(F)F)c3c(Cl)cccc32)n1]

7-Chloro-3-(4,6-dimethoxy-1,3,5-triazin-2-yl)-1,3-dihydro-2H-indol-2-one (6.0 g) is introduced as initial charge in 150 ml of dichloromethane. 1-Methyl-1H-imidazole (6.3 g) and 1,4-dimethylpiperazine (4.4 g) are added and the reaction mixture is stirred for one hour at room temperature. The mixture is cooled to −60° C. under nitrogen, and difluoromethanesulfonyl chloride (14.4 g) is slowly added dropwise with stirring, during which the temperature is kept below −50° C. The mixture is heated to −15° C. and held for two days at this temperature with occasional stirring.

For the work-up, 50 ml of water is added and the organic solvent is largely distilled off in vacuo. The residue is filtered, washed with water, taken up in 100 ml of 2-propanol, after-stirred for one hour, filtered, washed with 2-propanol and methanol and dried. This gives the title compound as a solid in an HPLC purity of 99% (5.2 g, 65% of theory). The UV absorption (maximum at 360 nm) and also 2D-NMR spectra verify the N-sulfonylation of the product.

LC-MS: M+H=421 (100%).

1H-NMR (400 MHz, CDCl$_3$): δ (ppm)=12.53 (s, 1H), 7.95 (dd, 1H), 7.13-7.21 (m, 2H), 6.96 (t, 1H), 4.21 (s, 3H), 4.16 (s, 3H).

The invention claimed is:

1. A process for preparing an N-sulfonyl-substituted oxindole of formula (3) which comprises a 6-ring heteroaryl substituent (Q) in the 3 position,

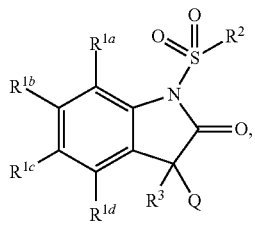

in which

R$^{1a}$ to R$^{1d}$, independently of one another, are selected from the group consisting of hydrogen, fluorine, chlorine, bromine, iodine, and also from (C$_1$-C$_6$)-alkyl, where the alkyl radical is branched or unbranched and is unsubstituted or is substituted by at least one substituent selected from the group consisting of fluorine, chlorine, (C$_1$-C$_4$)-alkoxy or (C$_3$-C$_7$)-cycloalkyl, (C$_3$-C$_7$)-cycloalkyl, where the cycloalkyl radical is unsubstituted or is substituted by at least one substituent selected from the group consisting of fluorine, chlorine, (C$_1$-C4)-alkyl or (C$_3$-C$_7$)-cycloalkyl or (C$_1$-C$_4$)-alkoxy, (C$_1$-C$_6$)-alkoxy, where the alkoxy radical is branched or unbranched and is unsubstituted or is substituted by at least one substituent selected from the group consisting of fluorine, chlorine, (C$_1$-C$_4$)-alkoxy or (C$_3$-C$_7$)-cycloalkyl, (C$_3$-C$_7$)-cycloalkoxy, where the cycloalkoxy radical is unsubstituted or is substituted by at least one substituent selected from the group consisting of fluorine, chlorine, (C$_1$-C$_4$)-alkyl or (C$_1$-C$_4$)-alkoxy, (C$_1$-C$_6$)-alkylthio, where the alkylthio radical is branched or unbranched and is unsubstituted or is substituted by at least one substituent selected from the group consisting of fluorine, chlorine, (C1-C4)-alkyl or (C1-C4)-alkoxy, (C$_3$-C$_7$)-cycloalkylthio, where the cycloalkylthio radical is unsubstituted or is substituted by at least one substituents selected from the group consisting of fluorine, chlorine, (C$_1$-C$_4$)-alkyl or (C$_1$-C$_4$)-alkoxy, and phenyl or 1-naphthyl or 2-naphthyl or a five- or six-membered heteroaromatic ring comprising from 1 to 2 heteroatoms, where said heteroatoms are selected, independently of one another, from the group consisting of 0 or N and where the aryl or heteroaryl radical is unsubstituted or is substituted by at least one substituent selected from the group consisting of fluorine, chlorine, bromine, iodine, (C$_1$-C$_4$)-alkyl, (C$_1$-C$_4$)-alkoxy or (C$_3$-C$_7$)-cycloalkyl or (C$_1$-C$_4$)-alkylthio, and R$_2$ is (C$_1$-C$_6$)-alkyl, where the alkyl radical is unsubstituted or is completely or partially substituted with fluorine, or (C$_3$-C$_7$)-cycloalkyl, where the cycloalkyl radical is unsubstituted or is completely or partially substituted with fluorine, R$^3$ is hydrogen or (C$_1$-C$_6$)-alkyl, where the alkyl radical is branched or unbranched and is unsubstituted or is substituted by at least one substituent selected from the group consisting of fluorine, chlorine, (C$_1$-C$_4$)-alkoxy or (C$_3$-C$_7$)-cycloalkyl, (C$_1$-C$_6$)-alkylthio, where the alkylthio radical is unsubstituted or is substituted by at least one substituents selected from the group consisting of fluorine, chlorine, (C$_1$-C$_4$)-alkyl or (C$_1$-C$_4$)-alkoxy, and Q is a six-membered heteroaromatic ring comprising from 1 to 3 nitrogen atoms, where the heteroaromatic ring is unsubstituted or is substituted by at least one substituent selected from the group consisting of (C$_1$-C$_4$)-alkyl, (C$_1$-C$_4$)-alkoxy or (C$_3$-C$_7$)-cycloalkyl or (C$_3$-C$_7$)-cycloalkoxy or (C$_1$-C$_4$)-alkylthio, said process comprising reacting of an oxindole compound of formula

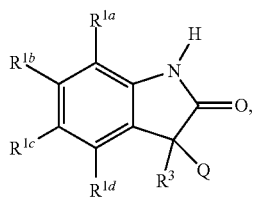

(1)

in which
R$^{1a}$ to R$^{1d}$, and R$^3$ and Q are as defined in formula (3), in a solvent with a sulfonyl compound (2)

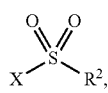

(2)

in which
R$^2$ is as defined in formula (3), and
X, as leaving group, is
fluorine, chlorine, bromine, 1-imidazolyl, 1H-benzotriazolyloxy, 1H-benzo-triazolyl or O—SO2-R$^7$, where R$^7$ is defined as R$^2$ and R$^2$ and R$^7$ are identical or different, or N(R8)SO$_2$R$^9$, where R$^8$ is carbonyl and R$^9$ is unsubstituted or substituted phenyl, and R$^8$ and R$^9$ are bonded with one another or are not bonded, where said reaction is carried out in the presence of an imidazole base substituted in the 1 position, or
a base mixture which comprises at least one imidazole base substituted in the
1 position.

2. The process for preparing an N-sulfonyl-substituted 3-triazinyloxindole of the formula (3-1) as claimed in claim 1

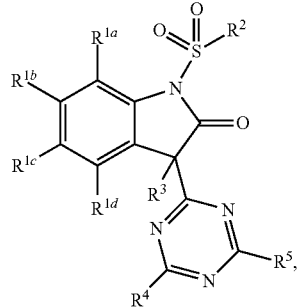

(3-1)

in which
R$^2$ is (C$_1$-C$_6$)-alkyl, or (C$_3$-C$_7$)-cycloalkyl, where the alkyl radical or the cycloalkyl radical is completely or partially substituted with fluorine, and
R$^4$ and R$^5$, independently of one another, are in each case hydrogen,
(C$_1$-C$_6$)-alkyl, where the alkyl radical is unsubstituted or is substituted by at least one substituent selected from the group consisting of fluorine, chlorine, (C$_1$-C$_4$)-alkoxy or (C$_3$-C$_7$)-cycloalkyl, (C$_1$-C$_6$)-alkoxy, where the alkoxy radical is branched or unbranched and is unsubstituted or is substituted by at least one substituent selected from the group consisting of fluorine, chlorine, (C$_1$-C$_4$)-alkoxy or (C$_3$-C$_7$)-cycloalkyl, with the proviso that compounds of formula (3-1), in which
R$^{1a}$ is fluorine and
R$^2$ is 2,2,-difluoroethyl or 1,1,1-trifluoroethyl,
are excluded.

3. The process as claimed in claim 1, where R$^3$ is hydrogen.

4. The process as claimed in claim 1, where R$^2$ is difluoromethane.

5. The process as claimed in claim 1, where the imidazole base substituted in the 1 position is at least one of
1-(C$_1$-C$_6$)-alkyl-1H-imidazole,
1-(C$_1$-C$_7$)-cycloalkyl-1H-imidazole,
1-benzyl-1H-imidazole,
1-aryl-1H-imidazole,
1-hetaryl-1H-imidazole, or
a mixture thereof.

6. The process as claimed in claim 5, where said imidazole base substituted in the 1 position, individually or in a mixture, comprises 1-methyl-1H-imidazole, 1-butyl-1H-imidazole or 1-benzyl-1H-imidazole.

7. The process as claimed in claim 1, where said base mixture is used and comprises at least one imidazole base substituted in the 1 position and additionally comprises at least one
tertiary amine base of formula (4) or

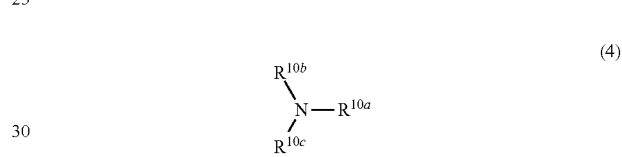

(4)

substituted pyridine base of formula (5) or

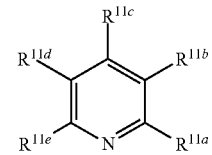

a mixture of a tertiary amine base of formula (4) and a substituted pyridine base of formula (5).

8. The process as claimed in claim 7, where the tertiary amine base is used and is at least one selected from the group consisting of:
diazabicyclo[2.2.2]octane (DABCO),
1-methylmorpholine,
1-ethylmorpholine
N,N-dimethylpiperazine and
1,2-bis(dimethylamino)ethane.

9. The process as claimed in claim 7, where said pyridine base is used and is 5-ethyl-2-methylpyridine or 3-methylpyridine.

10. The process as claimed in claim 1, where said reaction takes place in at least one of the solvents
dichloromethane,
2-methyltetrahydrofuran, or
ethyl acetate, or
in a mixture thereof.

11. The process as claimed in claim 1, where the addition of reactants takes place in one portion or in at least two portions over a period of from 0.05 to 6 hours.

12. The process as claimed in claim 1, where reaction temperature of sulfonylation is in a range from −20° C. to +10° C.

13. An N-sulfonyl-substituted 3-triazinyloxindole of formula (3-1)

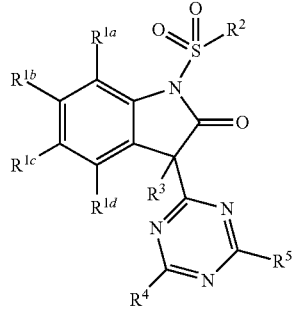

or a salt thereof (3-1a)

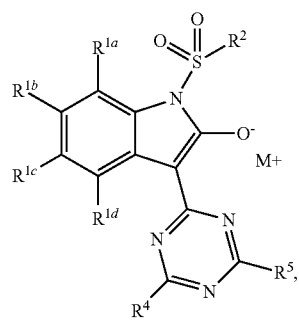

in which, in each case, $R^{1a}$ to $R^{1d}$, independently of one another, are selected from the group consisting of hydrogen, fluorine, chlorine, bromine, iodine, and also of ($C_1$-$C_6$)-alkyl, where the alkyl radical is branched or unbranched and is unsubstituted or is substituted by at least one or more substituent selected from the group consisting of fluorine, chlorine, ($C_1$-$C_4$)-alkoxy or ($C_3$-$C_7$)-cycloalkyl, ($C_3$-$C_7$)-cycloalkyl, where the cycloalkyl radical is unsubstituted or is substituted by at least one substituent selected from the group consisting of fluorine, chlorine, ($C_1$-$C_4$)-alkyl or ($C_3$-$C_7$)-cycloalkyl or ($C_1$-$C_4$)-alkoxy, ($C_1$-$C_6$)-alkoxy, where the alkoxy radical is branched or unbranched and is unsubstituted or is substituted by at least one substituent selected from the group consisting of fluorine, chlorine, ($C_1$-$C_4$)-alkoxy or ($C_3$-$C_7$)-cycloalkyl, ($C_3$-$C_7$)-cycloalkoxy, where the cycloalkoxy radical is unsubstituted or is substituted by at least one substituent selected from the group consisting of fluorine, chlorine, ($C_1$-$C_4$)-alkyl or ($C_1$-$C_4$)-alkoxy, ($C_1$-$C_6$)-alkylthio, where the alkylthio radical is branched or unbranched and is unsubstituted or is substituted by at least one or more substituent selected from the group consisting of fluorine, chlorine, ($C_1$-$C_4$)-alkyl or ($C_1$-$C_4$)-alkoxy, ($C_3$-$C_7$)-cycloalkylthio, where the cycloalkylthio radical is unsubstituted or is substituted by at least one or more substituent selected from the group consisting of fluorine, chlorine, ($C_1$-$C_4$)-alkyl or ($C_1$-$C_4$)-alkoxy, and phenyl or 1-naphthyl or 2-naphthyl or a five- or six-membered heteroaromatic ring comprising from 1 to 2 heteroatoms, where said heteroatoms, independently of one another, are selected from the group consisting of 0 or N, and where the aryl or heteroaryl radical is unsubstituted or is substituted by at least one substituent selected from the group consisting of fluorine, chlorine, bromine, iodine, ($C_1$-$C_4$)-alkyl, ($C_1$-$C_4$)-alkoxy or ($C_3$-$C_7$)-cycloalkyl or ($C_1$-$C_4$)-alkylthio, and $R^2$ is methyl, where the methyl is completely or partially substituted with fluorine, or ($C_3$-$C_7$)-cycloalkyl, where the cycloalkyl radical is completely or partially substituted with fluorine, R3 is hydrogen, or ($C_1$-$C_6$)-alkyl, where the alkyl radical is branched or unbranched and is unsubstituted or is substituted by at least one substituent selected from the group consisting of fluorine, chlorine, ($C_1$-$C_4$)-alkoxy or ($C_3$-$C_7$)-cycloalkyl, ($C_1$-$C_6$)-alkylthio, where the alkylthio radical is unsubstituted or is substituted by at least one substituent selected from the group consisting of fluorine, chlorine, ($C_1$-$C_4$)-alkyl or ($C_1$-$C_4$)-alkoxy, $R^4$ and $R^5$, independently of one another, are in each case hydrogen, ($C_1$-$C_6$)-alkyl, where the alkyl radical is unsubstituted or is substituted by at least one substituent selected from the group consisting of fluorine, chlorine, ($C_1$-$C_4$)-alkoxy or ($C_3$-$C_7$)-cycloalkyl, ($C_1$-$C_6$)-alkoxy, where the alkoxy radical is branched or unbranched and is unsubstituted or is substituted by at least one substituent selected from the group consisting of fluorine, chlorine, ($C_1$-$C_4$)-alkoxy or ($C_3$-$C_7$)-cycloalkyl, where, in the salt of formula (3-1a), M is Li, Na, K, Cs, Ba, Mg, Ca, Zn or $N(R^c)_4$, where $R^c$=H or $C_1$-$C_6$ alkyl, and where the number of counterions M+ is determined by a particular charge, such that an overall neutral compound of the formula (3-1a) is formed.

14. The N-sulfonyl-substituted 3-triazinyloxindole of the formula (3-1) or a salt of the formula (3-1a) as claimed in claim 13, where $R^{1a}$ to $R^{1d}$, independently of one another, are selected from the group consisting of hydrogen, fluorine, chlorine, and also from ($C^1$-$C^6$)-alkyl, where the alkyl radical is branched or unbranched, ($C^1$-$C^6$)-alkoxy, where the alkoxy radical is branched or unbranched, and $R^2$ is difluoromethyl or trifluoromethyl, $R^3$ is hydrogen, $R^4$ and $R^5$, independently of one another, are in each case ($C_1$-$C_4$)-alkyl, where the alkyl radical is branched or unbranched, ($C_1$-$C_4$)-alkoxy, where the alkoxy radical is branched or unbranched, where, in the salt of the formula (3-1a), M is Na and/or K.

15. The N-sulfonyl-substituted 3-triazinyloxindole of the formula (3-1) or a salt of the formula (3-1a) as claimed in claim 14, where $R^{1a}$ to $R^{1d}$, independently of one another, are selected from the group consisting of hydrogen, fluorine, chlorine, methoxy, and $R^2$ is difluoromethyl, $R^3$ is hydrogen, and $R^4$ and $R^5$, independently of one another, are in each case methoxy.

16. The N-sulfonyl-substituted 3-triazinyloxindole of the formula (3-1) a salt of the formula (3-1a) as claimed in claim 15, where $R^{1a}$ to $R^{1d}$, independently of one another, are selected from the group consisting of hydrogen and fluorine.

* * * * *